US011110136B2

(12) United States Patent
Mogna

(10) Patent No.: US 11,110,136 B2
(45) Date of Patent: Sep. 7, 2021

(54) COMPOSITION COMPRISING LACTIC ACID BACTERIA FOR USE IN THE PREVENTIVE AND/OR CURATIVE TREATMENT OF RECURRENT CYSTITIS

(71) Applicant: PROBIOTICAL S.P.A., Novara (IT)

(72) Inventor: Giovanni Mogna, Novara (IT)

(73) Assignee: PROBIOTICAL S.P.A., Novara (IT)

( * ) Notice: Subject to any disclaimer, the term of this patent is extended or adjusted under 35 U.S.C. 154(b) by 0 days.

(21) Appl. No.: 14/891,306

(22) PCT Filed: May 14, 2014

(86) PCT No.: PCT/IB2014/000731
§ 371 (c)(1),
(2) Date: Nov. 13, 2015

(87) PCT Pub. No.: WO2014/184639
PCT Pub. Date: Nov. 20, 2014

(65) Prior Publication Data
US 2016/0106787 A1 Apr. 21, 2016

(30) Foreign Application Priority Data
May 14, 2013 (IT) .......................... MI2013A000793

(51) Int. Cl.
| A61K 35/747 | (2015.01) |
| A61P 13/02 | (2006.01) |
| A61P 13/10 | (2006.01) |
| A61P 13/00 | (2006.01) |
| A61K 36/45 | (2006.01) |
| C12N 1/20 | (2006.01) |
| A61K 35/744 | (2015.01) |
| C12R 1/225 | (2006.01) |
| C12R 1/25 | (2006.01) |

(52) U.S. Cl.
CPC .......... *A61K 35/747* (2013.01); *A61K 35/744* (2013.01); *A61K 36/45* (2013.01); *A61P 13/00* (2018.01); *A61P 13/02* (2018.01); *A61P 13/10* (2018.01); *C12N 1/205* (2021.05); *C12R 2001/225* (2021.05); *C12R 2001/25* (2021.05); *Y02A 50/30* (2018.01)

(58) Field of Classification Search
CPC .... A61K 35/747; A61K 35/744; A61K 36/45; C12R 1/225; C12R 1/25; A61P 13/00; A61P 13/10; A61P 13/02; A61P 31/04; A61P 29/00; Y02A 50/30
See application file for complete search history.

(56) References Cited

U.S. PATENT DOCUMENTS

| 3,819,383 A | 6/1974 | Squire et al. |
| 3,819,838 A | 6/1974 | Smith et al. |
| 4,187,321 A | 2/1980 | Mutai et al. |
| 4,332,790 A | 6/1982 | Sozzi et al. |
| 4,670,272 A | 6/1987 | Chen et al. |
| 4,853,211 A | 8/1989 | Kurobe et al. |
| 5,071,976 A * | 12/1991 | Stirling ..................... C08L 5/00 435/101 |
| 5,343,672 A | 9/1994 | Kearney et al. |
| 5,413,960 A | 5/1995 | Dobrogosz et al. |
| 5,466,463 A | 11/1995 | Ford |
| 6,221,404 B1 | 4/2001 | Nguyen et al. |
| 6,262,019 B1 | 7/2001 | Keller et al. |
| 6,277,370 B1 | 8/2001 | Cavaliere Ved. Vesely et al. |
| 6,479,051 B1 | 12/2002 | Bruce et al. |
| 6,706,347 B1 | 3/2004 | Kurzinger et al. |
| 8,257,693 B2 * | 9/2012 | Ranganathan ....... A61K 31/702 424/738 |
| 9,005,682 B2 | 4/2015 | Sprenger et al. |
| 9,125,768 B2 | 9/2015 | Husmark et al. |
| 9,492,377 B2 | 11/2016 | Mogna et al. |
| 9,883,692 B2 | 2/2018 | Hougee et al. |
| 9,925,224 B2 | 3/2018 | Mogna et al. |
| 10,028,982 B2 | 7/2018 | Mogna |
| 10,286,017 B2 | 5/2019 | Mogna et al. |
| 10,384,847 B2 | 8/2019 | Mogna |
| 10,982,184 B2 | 4/2021 | Mogna et al. |
| 2002/0022019 A1 | 2/2002 | Laulund |
| 2002/0044968 A1 | 4/2002 | Van Lengerich |
| 2003/0118571 A1 | 6/2003 | Reid et al. |
| 2004/0185032 A1 | 9/2004 | Burrell |
| 2004/0208863 A1 | 10/2004 | Versalovic et al. |
| 2005/0017013 A1 | 1/2005 | Peisach et al. |
| 2005/0031814 A1 | 2/2005 | Dawes |
| 2005/0095232 A1 | 5/2005 | Volkmann |

(Continued)

FOREIGN PATENT DOCUMENTS

| CA | 2221426 A | 5/1998 |
| CA | 2739345 A1 | 4/2010 |

(Continued)

OTHER PUBLICATIONS

Vicariotto-2, published in Journal of Clinical Gastroenterology, vol. 48, Supp. 1, S96-S101, Nov. 2014.*
Terris et al., Urology 57(1): 26-29, 2001.*
Broadbent et al., J. Dairy Sci. 86:407-423, 2003.*
Darouiche et al., CID 41:1531-1534, 2005.*
Del Piano et al., presented in the 7th Probiotics, Prebiotics & New Foods Meeting held in Rome on Sep. 8-10, 2013, published in Journal of Clinical Gastroenterology, 48/Suppl 1: S56-61, 2014 (Year: 2013).*
International Search Report issued for International Application No. PCT/IB2014/000731 filed on May 14, 2014 in the name of Probiotical S.P.A. dated Jul. 25, 2014.

(Continued)

*Primary Examiner* — Allison M Fox
*Assistant Examiner* — Qing Xu
(74) *Attorney, Agent, or Firm* — Steinfl + Bruno LLP

(57) ABSTRACT

A composition comprising lactic bacteria for use in the preventive and/or curative treatment of bacterial infections, which cause urinary tract and/or bladder inflammations is described. The composition is in particular for the treatment of recurrent cystitis.

19 Claims, 2 Drawing Sheets

(56) References Cited

U.S. PATENT DOCUMENTS

| | | |
|---|---|---|
| 2005/0220776 A1 | 10/2005 | Brondstad et al. |
| 2006/0039973 A1 | 2/2006 | Aldritt et al. |
| 2006/0121571 A1 | 6/2006 | Klaenhammer et al. |
| 2006/0233774 A1 | 10/2006 | Lim et al. |
| 2007/0122397 A1 | 5/2007 | Sanguansri et al. |
| 2007/0148149 A1 | 6/2007 | Boettner et al. |
| 2007/0207132 A1 | 9/2007 | Speelmans et al. |
| 2007/0269515 A1 | 11/2007 | Henriksen et al. |
| 2008/0175899 A1 | 7/2008 | Ross et al. |
| 2008/0187628 A1 | 8/2008 | Champion et al. |
| 2008/0193485 A1 | 8/2008 | Gorbach et al. |
| 2008/0299099 A1 | 12/2008 | Heczko et al. |
| 2009/0041736 A1 | 2/2009 | Sprenger et al. |
| 2009/0061164 A1 | 3/2009 | Pasbrig et al. |
| 2009/0170185 A1 | 7/2009 | Hayakawa et al. |
| 2009/0175843 A1* | 7/2009 | Gans ............... A61K 31/375 424/94.65 |
| 2009/0180999 A1 | 7/2009 | Minatelli et al. |
| 2009/0226548 A1* | 9/2009 | Minatelli ............ A61K 36/45 424/732 |
| 2009/0252709 A1 | 10/2009 | Nose et al. |
| 2009/0294319 A1 | 12/2009 | Nageli et al. |
| 2010/0003369 A1 | 1/2010 | Ter Haar et al. |
| 2010/0092240 A1 | 4/2010 | Glasser |
| 2010/0092440 A1 | 4/2010 | Strozzi et al. |
| 2010/0168056 A1 | 7/2010 | Troup et al. |
| 2010/0278781 A1 | 11/2010 | Hougee et al. |
| 2011/0020400 A1 | 1/2011 | MacSharry et al. |
| 2011/0177198 A1 | 7/2011 | Songisepp et al. |
| 2011/0178488 A1 | 7/2011 | Balazs |
| 2011/0236360 A1 | 9/2011 | Ochi et al. |
| 2011/0274722 A1 | 11/2011 | Gorbach et al. |
| 2012/0058095 A1 | 3/2012 | Strozzi et al. |
| 2012/0195868 A1 | 8/2012 | Lathan et al. |
| 2012/0207929 A1 | 8/2012 | Yoo et al. |
| 2014/0065115 A1 | 3/2014 | Mogna et al. |
| 2014/0065116 A1 | 3/2014 | Mogna et al. |
| 2014/0072543 A1 | 3/2014 | Mogna |
| 2014/0093479 A1 | 4/2014 | Mogna et al. |
| 2014/0105874 A1 | 4/2014 | Mogna et al. |
| 2014/0127164 A1 | 5/2014 | Mogna et al. |
| 2014/0231300 A1 | 8/2014 | Mogna |
| 2014/0328932 A1 | 11/2014 | Mogna |
| 2015/0017128 A1 | 1/2015 | Mogna |
| 2015/0174179 A1 | 6/2015 | Sprenger et al. |
| 2016/0184372 A1 | 6/2016 | Mogna |
| 2017/0014335 A1 | 1/2017 | Mogna et al. |
| 2018/0236014 A1 | 8/2018 | Mogna et al. |
| 2019/0216864 A1 | 7/2019 | Mogna et al. |
| 2020/0325440 A1 | 10/2020 | Mogna et al. |

FOREIGN PATENT DOCUMENTS

| | | | |
|---|---|---|---|
| CN | 1233474 A | | 11/1999 |
| CN | 1345589 A | | 4/2002 |
| CN | 1853508 A | | 11/2006 |
| CN | 101432007 A | | 5/2009 |
| CN | 101801220 A | | 8/2010 |
| CN | 105163747 A | | 12/2015 |
| CN | 105377277 A | | 3/2016 |
| EA | 200200287 A1 | | 6/2002 |
| EA | 11952 B1 | | 9/2004 |
| EA | 10981 B1 | | 2/2007 |
| EP | 0002692 A1 | | 7/1979 |
| EP | 0845350 A1 | | 6/1998 |
| EP | 956858 A1 | | 11/1999 |
| EP | 1600060 A1 | | 11/2005 |
| EP | 1600061 A1 | | 11/2005 |
| EP | 1840205 A1 | | 10/2007 |
| EP | 2000530 A1 | | 12/2008 |
| EP | 2210505 A1 | | 7/2010 |
| EP | 2 269 465 A1 | | 1/2011 |
| EP | 2 338 976 A1 | | 6/2011 |
| EP | 2360237 A1 | | 8/2011 |
| EP | 2364712 A | * | 9/2011 |
| EP | 2 626 076 A1 | | 8/2013 |
| EP | 2707477 B1 | | 7/2018 |
| GB | 2396811 A | * | 7/2004 |
| JP | H11504049 A | | 4/1999 |
| JP | 2001258549 A | | 9/2001 |
| JP | 200250872 A | | 3/2002 |
| JP | 2002507123 A | | 3/2002 |
| JP | 2003522731 A | | 7/2003 |
| JP | 2006180836 A | | 7/2006 |
| JP | 2006519014 A | | 8/2006 |
| JP | 2008529535 A | | 8/2008 |
| JP | 2009511506 A | | 3/2009 |
| JP | 2009520470 A | | 5/2009 |
| JP | 2010511033 A | | 4/2010 |
| JP | 2010187670 A | | 9/2010 |
| JP | 2013009681 A | * | 1/2013 |
| JP | 2016518441 A | | 6/2016 |
| KR | 20130038395 A | | 4/2013 |
| KZ | 11784 A | | 8/2002 |
| KZ | 17967 B | | 6/2011 |
| RU | 2150268 C1 | | 6/2000 |
| RU | 2203946 C1 | | 5/2003 |
| RU | 2215656 C2 | | 11/2003 |
| RU | 2303058 C2 | | 7/2007 |
| RU | 2316586 C2 | | 2/2008 |
| RU | 2338511 C2 | | 11/2008 |
| RU | 2007/147945 A | | 7/2009 |
| RU | 2008/118418 A | | 11/2009 |
| RU | 2373274 C1 | | 11/2009 |
| RU | 2388479 C1 | | 5/2010 |
| RU | 2445073 C2 | | 3/2012 |
| RU | 2465320 C2 | | 10/2012 |
| WO | 94/12142 A1 | | 6/1994 |
| WO | 97/29762 A1 | | 8/1997 |
| WO | 97/29763 A1 | | 8/1997 |
| WO | 99/49877 A2 | | 10/1999 |
| WO | 00/35465 A2 | | 6/2000 |
| WO | 00/35465 A3 | | 12/2000 |
| WO | 00/72855 A2 | | 12/2000 |
| WO | 03090546 A1 | | 11/2003 |
| WO | 2004/089278 A2 | | 10/2004 |
| WO | 2004/101770 A1 | | 11/2004 |
| WO | 2006/013588 A1 | | 2/2006 |
| WO | 2006/073329 A1 | | 7/2006 |
| WO | 2006/082824 A1 | | 8/2006 |
| WO | 2006/091103 A2 | | 8/2006 |
| WO | 2007/020884 A1 | | 2/2007 |
| WO | 2007/029773 A1 | | 3/2007 |
| WO | 2007/050656 A2 | | 5/2007 |
| WO | 2007/100765 A2 | | 9/2007 |
| WO | 2007/125558 A1 | | 11/2007 |
| WO | 2008/038075 A1 | | 4/2008 |
| WO | 2008/065492 A2 | | 6/2008 |
| WO | 2008/107746 A2 | | 9/2008 |
| WO | 2008/153377 A1 | | 12/2008 |
| WO | 2009/138218 A1 | | 11/2009 |
| WO | 2010/023248 A1 | | 3/2010 |
| WO | 2010/033768 A1 | | 3/2010 |
| WO | 2010/038714 A1 | | 4/2010 |
| WO | 2010/099824 A1 | | 9/2010 |
| WO | 2010/103374 A2 | | 9/2010 |
| WO | 2010/128084 A1 | | 11/2010 |
| WO | 2010/133761 A1 | | 11/2010 |
| WO | 2011/012932 A1 | | 2/2011 |
| WO | 2011/017040 A1 | | 2/2011 |
| WO | 2011/044934 A1 | | 4/2011 |
| WO | WO 2011/11091 A | * | 9/2011 |
| WO | 2012/001440 A1 | | 1/2012 |
| WO | 2012/101500 A1 | | 8/2012 |
| WO | 2012/123770 A1 | | 9/2012 |
| WO | 2012/143787 A1 | | 10/2012 |
| WO | 2012/153179 A1 | | 11/2012 |
| WO | 2013/034974 A1 | | 3/2013 |
| WO | 2013/034975 A1 | | 3/2013 |
| WO | 2013/136891 A1 | | 3/2013 |
| WO | 2013/050831 A1 | | 4/2013 |
| WO | 2013/050833 A1 | | 4/2013 |

(56) References Cited

FOREIGN PATENT DOCUMENTS

| | | |
|---|---|---|
| WO | 2014/023995 A1 | 2/2014 |
| WO | 2014/184639 A1 | 11/2014 |
| WO | 2014/184643 A1 | 11/2014 |

OTHER PUBLICATIONS

Written Opinion issued for International Application No. PCT/IB2014/000731 filed on May 14, 2014 in the name of Probiotical S.P.A. dated Jul. 25, 2014.

Saggioro, A. "Probiotics in the Treatment of Irritable Bowel Syndrome." Journal of Clinical Gastroenterology, vol. 38(6), pp. S104-106. Jul. 2004.

Mogna, L. et al. "Assessment of the in vitro inhibitory activity of specific probiotic bacteria against different *Escherichia coli* strains." Journal of Clinical Gastroenterology, vol. 46, Supp. 1, pp. S29-S32. Oct. 2012.

Castro-Leyva, V. et al. "Preserved Ex Vivo Inflammatory Status in Decidual Cells from Women with Preterm Labor and Subclinical Intrauterine Infection." PLOS ONE, vol. 7 (8), e43605, pp. 1-6. Aug. 2012.

Al-Wahsh, I. et al. "Acute probiotic ingestion reduces gastrointestinal oxalate absorption in healthy subjects." Urological Research: A Journal of Clinical and Laboratory Investigation in Urolithiasis and Related Areas, vol. 40(3), pp. 191-196. Aug. 2011.

Hoesl, C. E. et al. "The Probiotic Approach: An Alternative Treatment Option in Urology" European Urology, vol. 47, No. 3, pp. 288-296. Mar. 2005.

Vicariotto, F. et al: "65: Effectiveness of an Association of a Cranberry Dried Extract, D-Mannose and The Three Microorganisms *L. plantarum* Lp01, *L. paracasei*, Lpc09 and *S. thermophilus* St10 in Women Affected by Cystitis: A Pilot Study", 7th Probiotics & Prebiotics New Foods, pp. 1-52, Jul. 2013.

"7th Probiotics & Prebiotics—new food", Universita Urbaniana, Rome. Poster 66: "Effectiveness of the Two Microorganisms *L. fermentum* LF15 and *L. plantarum* LP01, Formulated in Slow Release Vaginal Tablets, in Women Affected by Bacterial Vaginosis (BV): A Pilot Study", pp. Cover-50, Jul. 2013.

"DeNol" 2009; found on the internet Mar. 29, 2016; www.rlsnet.ru/tn_index_id_6426.htm; 6 pages (Russian original + English translation of relevant parts).

"Sachet" Webpage from merriam-webster.com, Oct. 7, 2011, accessed via WayBackMachine.com. 1 page.

Alam, M. et al. "Development and Evaluation of Acid-buffering Bioadhesive Vaginal Tablet for Mixed Vaginal Infections" AAPS PharmSciTech 2007; vol. 8; No. 4; Article 109, pp. E1-E8.

Aloisio et al. "Characterization of *Bifidobacterium* spp. Strains for the treatment of enteric disorders in newborns" Appl. Microbiol. Biotechnol., 2012, vol. 96, pp. 1561-1576 + 1 supplemental page.

Amaretti, et al. "Antioxidant properties of potentially probiotic bacteria: in vitro and in vivo activities", Applied Microbiology and Biotechnology. vol. 97 (2), 2013, pp. 809-817.

Antao et al. "The chicken as a natural model for extraintestinal infections caused by avian pathogenic *Escherichia coli* (APEC)" Microbial Pathogenesis, Nov.-Dec. 2008, vol. 45, No. 5-6, pp. 361-369—Abstract Only.

Baluka et al. "PCR-Based Detection of Genes Responsible for Oxalate Detoxification in Probiotic Microorganisms" Eastern Illinois University, Department of Biological Sciences.

Barber et al. "Strengths and Limitations of Model Systems for the Study of Urinary Tract Infections and Related Pathologies" Microbiology and Molecular Biology Reviews, Jun. 2016, vol. 80, No. 2, pp. 351-367.

Bespalov, V.G. et al. "Biologically active food supplements" Kafedra, 2000; pp. 38-47 (Russian original + English translation of relevant parts).

Best et al. "Models for the study of Clostridium difficile infection" Gut Microbes, Mar.-Apr. 2012, vol. 3, No. 2, pp. 145-167.

Bordoni, A. et al. "Cholesterol-lowering probiotics: in vitro selection and in vivo testing of bifidobacteria" Applied Microbiology and Biotechnology. Sep. 2013. vol. 97, No. 18, pp. 8273-8281.

Breach Action Filed by the General Secretary of the Andean Community Against the Republic of Peru, Process 89-AI-2000 (Gaceta Oficial, del Acuerdo de Cartagena, Sumario, Tribunal de Justicia de la Comunidad Andina), Ano XVIII, Numero 722, Lima, Oct. 12, 2001, 44 pgs. Spanish with English Abstract.

Briczinski, E. et al. "Strain-Specific Genotyping of *Bifidobacterium animalis* subsp. Lactis by Using Single-Nucleotide Polymorphisms, Insertions, and Deletions" Applied and Environmental Microbiology. Dec. 2009. vol. 75, No. 23, pp. 7501-7508.

Busch et al. "A Model of Infected Burn Wounds Using *Escherichia coli* O18:K1:H7 for the Study of Gram-Negative Bacteremia and Sepsis" Infection and Immunity, Jun. 2000, vol. 68, No. 6, pp. 3349-3351.

Candela, et al. "High taxonomic level fingerprint of the human intestinal microbiota by Ligase Detection Reaction—Universal Array approach" BMC Microbiology; 2010; vol. 10; No. 116; 16 pages.

Candela, et al. "Interaction of probiotic Lactobacillus and Bifidobacterium strains with human intestinal epithelial cells: Adhesion properties, competition against enteropathogens and modulation of IL-8 production", International Journal of Food Microbiology, vol. 125 (3), pp. 286-292, Jul. 2008.

Champagne, et al: "The determination of viable counts in probiotic cultures microencapsulated by spray-coating", Food Microbiology, Academic Press Ltd, London, GB, vol. 27, No. 8, Dec. 1, 2010 (Dec. 1, 2010), pp. 1104-1111. Abstract Only.

Cheikhyoussef, et al. "Antimicrobial activity and partial characterization of bacteriocin-like inhibitory substances (BLIS) produced by Bifidobacterium infantis BCRC 14602", Food Control, Butterworth, London, GB, vol. 20 (6), pp. 553-559, Jun. 2009.

Chen et al. "Probiotic Lactobacillus casei Expressing Human Lactoferrin Elevates Antibacterial Activity in the Gastrointestinal Tract" Biometals, 2010, vol. 23, pp. 543-554.

Chilean First Examination report dated Mar. 9, 2016 for Chilean application No. 2013-002148 filed on Jul. 26, 2013 in the name of Probiotical S.P.A., 21 pgs. Spanish with English translation.

Collado, et al: "Probiotic Strains and Their Combination Inhibit In Vitro Adhesion of Pathogens to Pig Intestinal Mucosa", Current Microbiology, Springer-Verlag, NE, vol. 55, No. 3, Jul. 25, 2007 (Jul. 25, 2007), pp. 260-265. Abstract Only.

Cremonini et al. "Effect of Different Probiotic Preparations on Anti-Helicobacter pylori Therapy-Related Side Effects: A Parallel Group, Triple Blind, Placebo-Controlled Study" Am. J. Gastroenterol.; 2002; vol. 97; pp. 2744-2749.

Del Piano, et al. "Evaluation of the intestinal colonization by microencapsulated probiotic bacteria in comparison with the same uncoated strains", Journal of Clinical Gastroenterology, vol. 44, pp. S42-S46, Sep. 2010.

Del Piano, et al. "Is microencapsulation the future of probiotic preparations? The increased efficacy of gastro-protected probiotics", Gut Microbes Mar.-Apr. 2011 LNKDPUBMED: 21637030, vol. 2, No. 2, Mar. 2011 (Mar. 2011), pp. 120-123.

Del Piano, M. et al. "Correlation between chronic treatment with Proton Pump Inhibitors (PPIs) and bacterial overgrowth in the stomach: any possible beneficial role for selected lactobacilli?" J. Clin. Gastroenterol., 48 Suppl 1: S40-6. 13 pgs. Nov.-Dec. 2014.

Dr. Jose Ma Sune Negre, New Galenic Formulations to Forms of Administration (Nuevas Aportaciones Galenicas a las Formas de Administracion. En: Curos de formacion continuada para farmaceuticos de hospital. Fundacion Promocion Medica. Barcelona, 2002, 3, pp. 27-65), 3.2. 27 pgs. Spanish with English Abstract.

Eaton, et al: "Probiotic Lactobacillus reuteri Ameliorates Disease Due to Enterohemorrhagic *Escherichia coli* in Germfree Mice", Infection and Immunity, vol. 79, No. 1, Oct. 25, 2010 (Oct. 25, 2010), 9 pages.

European Commission—Health & Consumer Protection Directorate—General, "Opinion of the Scientific Committee on Animal Nutrition on the Criteria for Assessing the Safety of Micro-Organisms Resistant to Antibiotics of Human Clinical and Veterinary Importance", 2002, pp. 1-20.

(56) References Cited

OTHER PUBLICATIONS

European Patent Office Communication pursuant to Article 94(3) EPC in relation to Application No. 12 780 278.3-1401. dated Jun. 6, 2015 4 pages.
FAO/WHO. Guidelines for the Evaluation of Probiotics in Food. Apr. 30/May 1, 2002, 11 pgs.
Federici, et al. "Characterization and Heterologous Expression of the Oxalyl Coenzyme A Decarboxylase Gene from Bifidobacterium lactic" Applied and Environmental Microbiology, Sep. 2004; vol. 70; No. 9; pp. 5066-5073.
Fernandez, et al: "Probiotic properties of human lactobacilli strains to be used in the gastrointestinal tract", Journal of Applied Microbiology, Oxford, GB, vol. 94, No. 3, Online Feb. 12, 2003, pp. 449-455.
First Examination Report dated Apr. 28, 2014 for NZ IP No. 614002 filed on Aug. 6, 2013 in the name of Probiotical S.P.A.
First Office Action for Chinese Patent Application No. 201180070870.0 dated Feb. 15, 2016. 15 pages. (Chinese original + English translation).
First Office Action for Chinese Patent Application No. 201280015994.3 dated Mar. 25, 2016. 23 pages. (Chinese original + English translation).
First Office Action for Chinese Patent Application No. 201280022854.9 dated Nov. 4, 2014 filed on May 9, 2012 in the name of Probiotical S.P.A. (English + Chinese). 15 pages.
Fourth Office Action for Chinese Patent Application No. 201280022854.9 dated Feb. 13, 2017 filed on May 9, 2012 in the name of Probiotical S.P.A. (English + Chinese). 12 pages.
Germond, J.E. et al. "Evolution of the bacterial species *Lactobacillus delbrueckii*: a partial genomic study with reflections on prokaryotic concept." Mol. Biol. Evol. vol. 20(10, pp. 93-104. Jan. 2003 (Abstract Only).
Gotteland, et al, "Systematic review: are probiotics useful in controlling gastric colonization by Helicobacter pylori?" Alimentary Pharmacology & Therapeutics, vol. 23, pp. 1077-1086, Apr. 15, 2006.
Grill et al. "Bile salt toxicity to some bifidobacteria strains: Role of conjugated bile salt hydrolase and pH" Canadian Journal of Microbiology. Oct. 2000, 46, pp. 878-884.
Grimoud, J. et al., "In vitro screening of probiotic lactic acid bacteria and prebiotic glucooligosaccharides to select effective synbiotics", Anaerobe, 16 (2010) 493-500.
Guardamagna et al. "Bifidobacteria supplementation: Effects on plasma lipid profiles in dyslipidemic children" Nutrition, 2014; vol. 30; pp. 831-836.
Gueimonde, et al: "Adhesion and competitive inhibition and displacement of human enteropathogens by selected lactobacilli", Food Research International, Elsevier Applied Science, Barking, GB, vol. 39, No. 4, May 1, 2006 (May 1, 2006), pp. 467-471. Summary Citation.
Guo, X. "Basics and Application of Probiotics" Science and Technology Press, 1st Version, Oct. 2002. 2 pages.
Guonong et al. China; Light Industry Press, 1st Edition in 2009, Publication Date: Aug. 31, 2009. pp. 363 (Chinese original + English excerpt).
Gurbuz et al. "Effect of N-Acetyl Cysteine on Helicobacter pylori" Souther Medical Journal; Nov. 2005; 2002; vol. 97; pp. 2744-2749.
Hamilton-Miller, "The role of probiotics in the treatment and prevention of Helicobacter pylori infection", International Journal of Antimicrobial Agents Oct. 2003 LNKD—PUBMED 14522098, vol. 22, No. 4, Oct. 2003, pp. 360-366, XP002661415.
Hütt, et al: "Antagonistic activity of probioitic lactobacilli and bifidobacteria aganst entero- and uropathogens", Journal of Applied Microbiology, vol. 100, No. 6, Jun. 2006 (Jun. 2006), pp. 1324-1332.
Huynh, et al: "N-Acetylcysteine, a Novel Treatment for Helicobacter pylori Infection", Digestive Diseases and Sciences, Kluwer Academic Publishers—Plenum Publishers, NE, vol. 49, No. 11-12, Nov. 1, 2004 (Nov. 1, 2004), pp. 1853-1861.
Japanese Patent Office Official Action for Japanese Patent Application No. 2013-550962, dated Dec. 1, 2015. 10 pages. (Japanese original + English translation).
Japanese Patent Office Official Action for Japanese Patent Application No. 2013-558517, dated Mar. 3, 2015. 4 pages. (Japanese original + English translation).
Japanese Patent Office Official Action for Japanese Patent Application No. 2014-509849, dated Apr. 26, 2016. 9 pages. (Japanese original + English translation).
Japanese Patent Office Official Action for Japanese Patent Application No. 2014-529081, dated May 31, 2016. 4 pages. (Japanese original + English translation).
Japanese Patent Office Official Action Summary for Japanese Patent Application No. 2014-509850 filed on behalf of Probiotical S.P.A. dated Feb. 16, 2016. (Japanese original + English translation) 5 pages.
Johnson-Henry, et al: "Lactobacillus rhamnosus Strain GG Prevents Enterohemorrhagic *Escherichia coli* O157:H7-Induced Changes in Epithelial Barrier Function", Infection and Immunity, vol. 76, No. 4, Apr. 1, 2008 (Apr. 1, 2008), pp. 1340-1348.
Karamanolis et al. "A Glass of Water Immediately Increases Gastric pH in Healthy Subjects" Dig. Dis Sci., 2008, vol. 53, pp. 3128-3132.
Keersmaecker et al. "Strong antimicrobial activity of Lactobacillus rhamnosus GG against *Salmonella typhimurium* is due to accumulation of lactic acid" Federation of European Microbiological Societies Microbiology Letters 259. (2006) 89-96.
Khavkin, A.I. et al. "Modern principles of ulcer disease" 2009; found on the internet Mar. 29, 2016; www.Ivrach.ru/2005/02/4532114/; 6 pages (Russian original + English translation of relevant parts).
Kim, et al. "Antimicrobial effect of Bifidobacterium breve and Bifidobacterium infantis against *Salmonella typhimurium* KCTC 1925 and *E. coli* O157:H7 ATCC 43895", Food Science and Biotechnology, Korean Society of Food Science and Technology, vol. 11 (1), pp. 89-92, Jan. 2002.
Kim, H.S. et al. "In vitro Antioxidative Properties of Lactobacilli" Asian-Aust. J. Anim. Sci. 2006; vol. 19; No. 2; pp. 262-265.
Kizerwetter-Swida et al. "Selection of Potentially Probiotic Lactobacillus Strains Towards their Inhibitory Activity against Poultry Enteropathogenic Bacteria" Polish Journal of Microbiology, 2005, vol. 54, No. 4, pp. 287-294.
Klaver et al. "The Assumed assimilation of cholesterol by lactobacilli and Bifidobacterium bifidum is due to their bile salt-deconjugating activity" Appl Environ Microbiology, 1993, vol. 59, No. 4, pp. 1120-1124.
Krosnyuk, I.I. et al. "Pharmaceutical technology: Technology of dosage forms: a textbook for university students" Academia editorial center; 2006; p. 6 47 (Russian original + English translation of relevant parts).
Lieske, et al. "Use of a probiotic to decrease enteric hyperoxaluria" Kidney International; 2005; vol. 68; pp. 1244-1249.
Likotrafiti, et al. "Molecular Identification and Anti-pathogenic Activities of Putative Probiotic Bacteria Isolated from Faeces of Healthy Elderly Individuals", Microbial Ecology in Health and Disease, 16, pp. 105-112 (2004).
Lin, et al., "Antioxidative effect of intestinal bacteria Bifidobacterium longum ATCC 15708 and Lactobacillus acidophilus ATCC 4356", Digestive Diseases & Sciences 2000, 45: 1617-1622.
Lin, et al., "Inhibition of lipid peroxidation by Lactobacillus acidophilus and Bifidobacterium longum", J. Agricultural & Food Chemistry 1999, 47: 3661-3664.
Liu, J-R. et al. "Antioxidative Activities of Kefir" Asian-Aust. J. Anim. Sci, 2005; vol. 18. No. 4; pp. 567-573.
Losada, et al. "Towards a healthier diet for the colon: the influence of fructooligosaccharides and lactobacilli on intestinal health", Nutrition Research, vol. 22, Jan. 2002, pp. 71-84.
Lu, et al: "New development in the mechanistic understanding of peptic ulcer diseases", Drug Discovery Today: Disease Mechanisms, Elsevier, vol. 3, No. 4, 2006, pp. 431-437.
Lutgendorff, et al., "Probiotics enhance pancreatic glutathione biosynthesis and reduce oxidative stress in experimental acute pancreatitis", Am. J. Physiol. Gastrointest. Liver Physiol., 2008, vol. 295; G1111-G1121.

(56) References Cited

OTHER PUBLICATIONS

MacFarland, S. et al., "Review article: prebiotics in the gastrointestinal tract", Alimentary Pharmacology & Therapeutics, 2006, 24, 701-714.
Malecka, "Antioxidant properties of the unsaponifiable matter isolated from tomato seeds, oat grains and wheat germ oil" Food Chemistry, 2002, vol. 79, pp. 327-330.
Marchese, et al.: "Effect of fosfomycin alone and in combination with N-acetylcysteine on *E. coli* biofilms", International Journal of Antimicrobial Agents, vol. 22, Oct. 1, 2003, Suppl. 2, (Oct. 1, 2003), pp. 95-100.—Abstract Only.
Masashi Okamura, "Youkei no Tomo", 2008, vol. 558, pp. 17-21 (Japanese original + English translation).
McFarland: "Meta-analysis of probiotics for the prevention of antibiotic associated diarrhea and the treatment of Clostridium difficile disease", The American Journal of Gastroenterology Apr. 2006 LNKD—PUBMED:16635227, vol. 101, No. 4, Apr. 2006 (Apr. 2006), pp. 812-822.
Mei, X. et al. "Manual of New Drug and Special Drug" Technology Press, 2nd Version, Jan. 2001.
Milani, C. et al., "Comparative Genomics of *Bifidobacterium animalis* subsp. lactis Reveals a Strict Monophyletic Bifidobacterial Taxon", Applied and Environmental Microbiology, 79 (14), 2013, 4304-4315.
Modesto, et al. "Resistance to freezing and freeze-drying storage processes of potential probiotic bifidobacteria", Annals of Microbiology, 54 (1), pp. 43-48 (2004).
Moen et al. "Testing the Efficacy and Toxicity of Adenylyl Cyclase Inhibitors against Enteric Pathogens Using In Vitro and In Vivo Models of Infection" Infection and Immunity, Apr. 2010, vol. 78, No. 4, pp. 1740-1749.
Mogna et al. "In Vitro Inhibition of Klebsiella pneumoniae by *Lactobacillus delbrueckii* Subsp. delbrueckii LDD01 (DSM 22106): An Innovative Strategy to Possibly Counteract Such Infections in Humans?" J. Clin. Gastroenterol. Nov.-Dec. 2016, vol. 50, Supp. 2, pp. S136-S139.
Office Action for Russian Patent Application No. 2013137656/15(056766) filed Jan. 24, 2012 on behalf of Probiotical S.P.A. dated Mar. 18, 2016. 10 pages (Russian original + English translation).
Office Action for Russian patent application No. 2014107771/10(012274) filed on behalf of Probiotical S.P.A. dated Jun. 2, 2016. 8 pages (Russian original + English translation).
Office Action Inquiry for Russian Patent Application No. 2013144267 filed Mar. 17, 2011 on behalf of Probiotical S.P.A. dated Mar. 12, 2015 5 pages. English Translation.
Office Action dated Jul. 15, 2014 for KZ Application No. 2013/1615.1 filed on Jan. 24, 2012 by Tagbergenova Alma Taishevna et al.
Official Action for Russian Patent Application No. 2013151611 filed Apr. 18, 2012 on behalf of Giovanni Mogna. 12 pages (Russian original + English translation).
Okombo, J. et al., "Probiotic-induced reduction of gastrointestinal oxalate absorption in healthy subjects", Urol Res (2010), 38: 169-178.
Opposition filed to Application No. SP-2013-12844. 14 pages. Spanish original with English Translation; Date of Notification: Nov. 17, 2015.
Ouoba, et al., "Resistance of potential probiotic lactic acid bacteria and bifidobacteria of African and European origin to antimicrobials: Determination and transferability of the resistance genes to other bacteria", International Journal of Food Microbiology, 2008, 121, 217-224.
Ouwehand, A. et al. "Probiotics: an Overview of beneficial effects" Antonie van Leeuwenhoek. 2002, vol. 82; pp. 279-289.
Pascual, L. et al. "Vaginal Colonization and Activity of the Probiotic Bacterium Lactobacillus Fermentum L23 in a Murine Model of Vaginal Tract Infection", Journal of Medical Microbiology, vol. 59, No. 3, pp. 360-364, Nov. 2009.
PCT International Search Report for PCT/IB2011/000561 filed on Mar. 17, 2011 in the name of Probiotical S.P.A. dated Dec. 16, 2011.
PCT International Search Report for PCT/IB2012/000095 filed on Jan. 24, 2012 in the name of Probiotical S.p.A. dated Mar. 29, 2012.
PCT International Search Report for PCT/IB2012/000779 filed on Apr. 18, 2012 in the name of Giovanni Mogna, dated Jul. 19, 2012.
PCT International Search Report for PCT/IB2012/000895 filed on May 9, 2012 in the name of Probiotical S.P.A. dated Sep. 21, 2012. 5 pages.
PCT International Search Report for PCT/IB2012/000897 filed on May 9, 2012 in the name of Probiotical S.P.A. dated Aug. 24, 2012.
PCT International Search Report for PCT/IB2012/000907 filed on May 9, 2012 in the name of Probiotical S.P.A. dated Sep. 27, 2012.
PCT International Search Report for PCT/IB2012/001741 filed on Sep. 10, 2012 in the name of Giovanni Mogna, dated Dec. 3, 2012.
PCT International Search Report for PCT/IB2012/001745 filed on Sep. 10, 2012 in the name of Probiotical S.p.A. dated Dec. 17, 2012.
PCT International Search Report for PCT/IB2012/001848 filed on Sep. 21, 2012 in the name of Probiotical S.P.A. dated Dec. 3, 2012.
PCT International Search Report for PCT/IB2014/000739 filed on May 14, 2014 in the name of Probiotical S.P.A. dated Jul. 31, 2014 8 pages.
International Preliminary Report on Patentability for PCT/IB2011/000561 filed on Mar. 17, 2011 in the name of Probiotical S.P.A. dated Sep. 17, 2013.
PCT IPRP for PCT/IB2012/000095 filed on Jan. 24, 2012 in the name of Probiotical S.p.A. dated Jul. 30, 2013.
International Preliminary Report on Patentability for PCT/IB2012/000895 filed on May 9, 2012 in the name of Probiotical S.P.A. dated Nov. 12, 2012. 7 pages.
International Preliminary Report on Patentability for PCT/IB2012/000897 filed on May 9, 2012 in the name of Probiotical S.P.A. dated Nov. 12, 2013.
PCT IPRP for PCT/IB2012/000907 filed on May 9, 2012 in the name of Probiotical S.P.A. dated Nov. 12, 2013.
PCT IPRP for PCT/IB2012/001745 filed on Sep. 10, 2012 in the name of Probiotical North America Inc. dated Mar. 12, 2014 8 pages.
PCT IPRP for PCT/IB2014/000739 filed on May 14, 2014 in the name of Probiotical S.P.A. dated Nov. 26, 2015. 15 pages.
PCT Written Opinion for PCT/IB2011/000561 filed on Mar. 17, 2011 in the name of Probiotical S.P.A. dated Dec. 16, 2011.
PCT Written Opinion for PCT/IB2012/000095 filed on Jan. 24, 2012 in the name of Probiotical S.p.A. dated Mar. 29, 2012.
PCT Written Opinion for PCT/IB2012/000779 filed on Apr. 18, 2012 in the name of Giovanni Mogna. dated Jul. 19, 2012.
PCT Written Opinion for PCT/IB2012/000895 filed on May 9, 2012 in the name of Probiotical S.P.A. dated Sep. 21, 2012.
PCT Written Opinion for PCT/IB2012/000897 filed on May 9, 2012 in the name of Probiotical S.P.A. dated Aug. 24, 2012.
PCT Written Opinion for PCT/IB2012/000907 filed on May 9, 2012 in the name of Probiotical S.P.A. dated Sep. 27, 2012.
PCT Written Opinion for PCT/IB2012/001741 filed on Sep. 10, 2012 in the name of Giovanni Mogna. dated Dec. 3, 2012.
PCT Written Opinion for PCT/IB2012/001745 filed on Sep. 10, 2012 in the name of Probiotical S.P.A. dated Dec. 17, 2012.
PCT Written Opinion for PCT/IB2012/001848 filed on Sep. 21, 2012 in the name of Probiotical S.P.A. dated Dec. 3, 2012.
PCT Written Opinion for PCT/IB2014/000739 filed on May 14, 2014 in the name of Probiotical S.P.A. dated Jul. 31, 2014 11 pages.
Peran, et al., A comparative study of the preventative effects exerted by three probiotics, Bifidobacterium lactis, Lactobacillus casei and Lactobacillus acidophilus, in the TNBS model of rat colitis, J. Applied Microbiology 2007, 103: 836-844.
Pina, et al., "Prevalence and dietetic management of mild gastrointestinal disorders in milk-fed infants", World Journal of Gastroenterology, 2008, vol. 14, No. 2: 248-254.
Puccio, G. et al."Clinical evaluation of a new starter formula for infants containing live Bifidobacterium longum BL999 and prebiotics" Nutrition 2007 vol. 23; pp. 1-8.
Qingbin et al. Science Press, 1st Edition, Publication Date: Jun. 30, 2012. pp. 118-123 (Chinese original + English excerpt).
Rada, et al. "Susceptibility of bifidobacteria to nisin", Letters in Applied Microbiology, vol. 26, 1998, pp. 123-125.

(56) References Cited

OTHER PUBLICATIONS

Rada, et al: "Susceptibility of bifidobacteria to lysozyme as a possible selection criterion for probiotic bifidobacterial strains", Biotechnology Letters, Springer Netherlands, Dordrecht, vol. 32, No. 3, Nov. 27, 2009 (Nov. 27, 2009), pp. 451-455. Abstract Only.
Ritchie "Animal Models of Enterohemorrhagic *Escherichia coli* Infection" Microbiology Spectrum, Aug. 15, 2014, 13 pages.
Ronnqvist, D. et al. "Lactobacillus fermentum Ess-1 with unique growth inhibition of vulvovaginal candidiasis pathogens", Journal of Medical Microbiology (2007), 56, pp. 1500-1504.
Santini et al. "Characterization of probiotic strains: An application as feed additives in poultry against Campylobacter jejuni" International Journal of Food Microbiology, 2010, vol. 141, pp. S98-S108.
Santini et al., "Characterization of probiotic strains: an application as feed additives in poultry against Campylobacter jejuni", Int J Food Microbiol., 2010, 141 Suppl 1:S98-108. Epub Apr. 8, 2010. Abstract Only.
Search Report and Written Opinion dated Nov. 11, 2011 for IT MI20110792 filed on May 9, 2011 in the name of Probiotical S.P.A. Second Office Action for Chinese Patent Application No. 201280034204.6 dated Oct. 21, 2016 filed in the name of Probiotical S.P.A. (English + Chinese). 17 pages.
Sgouras Dionyssios N, et al., "Lactobacillus johnsonii La1 attenuates Helicobacter pylori-associated gastritis and reduces levels of proinflammatory chemokines in C57BL/6 mice", Clinical and Diagnostic Laboratory Immunology, American Society for Microbiology, US, vol. 12, No. 12, Dec. 1, 2005, pp. 1378-1386.
Shigeru Kamiya, "Igaku no Ayumi" Journal of Clinical and Experimental Medicine, 2003; vol. 207; No. 10, pp. 894-898 (Japanese original + English translation).
Shim et al. "Antimicrobial activity of lactobacillus strains against uropathogens" Pediatrics International, 2016, vol. 58, pp. 1009-1013.
Shu, Q. et al. "Immune protection mediated by the probiotic Lactobacillus rhamnosus HN001 (DR20) against *Escherichia coli* O157:H7 infection in mice" FEMS Immunology and Medical Microbiology. 2002, 34, 59-64.
Strus, M. et al. "Studies on the Effects of Pro Biotic Lactobacillus Mixture Given Orally on Vaginal and Rectal Colonization and on Parameters of Vaginal Health in Women with Intermediate Vaginal Flora" Eurpoean Journal of Obstetrics Gynecology and Reproductive Biology, vol. 163, No. 2 pp. 210-215. Aug. 2012.
The EFSA Journal, "Opinion of the Scientific Panel on Additives and Products or Substances used in Animal Feed on the updating of the criteria used in the assessment of bacteria for resistance to antibiotics of human and veterinary importance", 2005, 223, pp. 1-12.
Third Office Action for Chinese Patent Application No. 201280022854. 9, dated May 17, 2016. 12 pages. (Chinese original + English translation).
Torriani, et al. "Differentiation of Lactobacillus plantarum, L. pentosus, and L. paraplantarum by recA Gene Sequence Analysis and Multiplex PCR Assay with recA Gene-Derived Primers", Appl. Environ. Microbiol. 2001. vol. 67 (8), pp. 3450-3454.
Tsai et al. "Three Lactobacillus strains from healthy infant stool inhibit enterotoxigenic *Escherichia coli* grown in vitro" Anaerobe, Apr. 2008, vol. 14, No. 2, pp. 61-67—Abstract Only.
Turroni, et al. "Oxalate consumption by lactobacilli: evaluation of oxalyl-CoA decarboxylase and formyl-CoA transferase activity in Lactobacillus acidophilus" Journal of Applied Microbiology; 2007; vol. 103; pp. 1600-1609.
Van Hemert, Et al. "Influence of the Multispecies Probiotic Ecologic Barrier on Parameters of Intestinal Barrier Function" Food and Nutrition Sciences, 2014, 5, pp. 1739-1745.
Vasiljevic et al., "Probiotics-From Metchnikoff to bioactives", International Dairy Journal, Elsevier Applied Science, Barking, GB, vol. 18, No. 7, Jul. 1, 2008, pp. 714-728, XP022701025.

Walter, et al. "Detection and Identification of Gastrointestinal *Lactobacillus* Species by Using Denaturing Gradient Gel Electrophoresis and Species-Specific PCR Primers", Appl. Environ. Microbiol. 2000. vol. 66 (1), pp. 297-303.
Wang Kuan-Yuan, et al: "Effects of ingesting Lactobacillus- and Bifidobacterium-containing yogurt in subjects-with colonized Helicobacter pylori", The American Journal of Clinical Nutrition, American Society for Nutrition, US, vol. 80, No. 3, Sep. 1, 2004, pp. 737-741.
Wikipedia "Pharmaceutical Drug" Updated Apr. 15, 2016. Downloaded from the internet Apr. 21, 2016. 11 pages.
Wikipedia, "Strain (biology)" https://en.wikipedia.org/wiki/Strain_(biology) Retrieved on Nov. 3, 2015. 2 pgs.
Search Report and Written Opinion dated Nov. 11, 2011 for IT MI20110792 filed on May 9, 2011 in the name of Probiotical S.P.A.. 9 pages.
Ying, et al: "Microencapsulated Lactobacillus rhamnosus GG Powders: Relationship of Powder Physical Properties to Probiotic Survival during Storage", Journal of Food Science, vol. 75, No. 9, Nov. 1, 2010 (Nov. 1, 2010), pp. E588-E595. Abstract Only.
Yoon, Y. et al. "Occurrence of Glutathione Sulphydryl (GSH) and Antioxidant Activities in Probiotic *Lactobacillus* spp." Asian-Aust. J. Anim. Sci, 2004; vol. 17; No. 11; pp. 1582-1585.
Yutaka Kanamori, Joumyaku Keichou Eiyou "Parenteral and Enteral Nutrition", 2010, vol. 25; No. 4, pp. 923-928 (Japanese original + English translation).
Zanoni, et al., Growth kinetics on oligo- and polysaccharides and promising features of three antioxidative potential probiotic strains, J. Applied Microbiology 2008, 105: 1266-1276.
Zhang, et al., "Evaluation of Lactobacillus rhamnosus GG using an *Escherichia coli* K88 model of piglet diarrhoea: Effects on diarrhoea incidence, faecal microflora and immune responses", Veterinary Microbiology, Elsevier BV. NL, vol. 141, No. 1-2, Feb. 24, 2010, pp. 142-148. Epub Sep 11, 2009. Abstract Only.
Restriction Requirement for U.S. Appl. No. 13/982,255, filed Nov. 12, 2013 on behalf of Giovanni Mogna, dated Oct. 17, 2014. 6 pages.
Non-Final Office Action for U.S. Appl. No. 13/982,255, filed Nov. 12, 2013 on behalf of Giovanni Mogna, dated Mar. 10, 2015. 19 pages.
Final Office Action for U.S. Appl. No. 13/982,255, filed Nov. 12, 2013 on behalf of Giovanni Mogna, dated Sep. 17, 2015. 15 pages.
Notice of Allowance for U.S. Appl. No. 13/982,255, filed Nov. 12, 2013 on behalf of Giovanni Mogna, dated Jan. 22, 2016. 10 pages.
Notice of Allowance for U.S. Appl. No. 13/982,255, filed Nov. 12, 2013 on behalf of Giovanni Mogna, dated Jun. 15, 2016. 11 pages.
Notice of Allowance for U.S. Appl. No. 13/982,255, filed Nov. 12, 2013 on behalf of Giovanni Mogna, dated Jul. 27, 2016. 9 pages.
Restriction Requirement for U.S. Appl. No. 14/005,821, filed Nov. 6, 2013 on behalf of Giovanni Mogna, dated Jan. 7, 2014. 7 pages.
Non-Final Office Action for U.S. Appl. No. 14/005,821, filed Nov. 6, 2013 on behalf of Giovanni Mogna, dated Jun. 5, 2014. 36 pages.
Final Office Action for U.S. Appl. No. 14/005,821, filed Nov. 6, 2013 on behalf of Giovanni Mogna, dated Dec. 30, 2014. 30 pages.
Restriction Requirement for U.S. Appl. No. 14/113,211, filed Nov. 26, 2013 on behalf of Giovanni Mogna, dated Sep. 5, 2014. 9 pages.
Non-Final Office Action for U.S. Appl. No. 14/113,211, filed Nov. 26, 2013 on behalf of Giovanni Mogna, dated Apr. 22, 2015. 13 pages.
Non-Final Office Action for U.S. Appl. No. 14/113,211, filed Nov. 26, 2013 on behalf of Giovanni Mogna, dated Jan. 22, 2016. 13 pages.
Final Office Action for U.S. Appl. No. 14/113,211, filed Nov. 26, 2013 on behalf of Giovanni Mogna, dated Nov. 22, 2016. 12 pages.
Restriction Requirement for U.S. Appl. No. 14/117,003, filed Dec. 27, 2013 on behalf of Giovanni Mogna, dated Feb. 20, 2015. 9 pages.
Non-Final Office Action for U.S. Appl. No. 14/117,003, filed Dec. 27, 2013 on behalf of Giovanni Mogna, dated Oct. 14, 2015. 18 pages.
Final Office Action for U.S. Appl. No. 14/117,003, filed Dec. 27, 2013 on behalf of Giovanni Mogna, dated Jun. 2, 2016. 11 pages.

(56) References Cited

OTHER PUBLICATIONS

Notice of Allowance for U.S. Appl. No. 14/117,003, filed Dec. 27, 2013 on behalf of Giovanni Mogna, dated Nov. 9, 2016. 7 pages.
Restriction Requirement for U.S. Appl. No. 14/116,999, filed Dec. 20, 2013 on behalf of Giovanni Mogna, dated Mar. 11, 2015. 12 pages.
Non-Final Office Action for U.S. Appl. No. 14/116,999, filed Dec. 20, 2013 on behalf of Giovanni Mogna, dated Jun. 16, 2015. 28 pages.
Non-Final Office Action for U.S. Appl. No. 14/116,999, filed Dec. 20, 2013 on behalf of Giovanni Mogna, dated Mar. 14, 2016. 25 pages.
Final Office Action for U.S. Appl. No. 14/116,999, filed Dec. 20, 2013 on behalf of Giovanni Mogna, dated Dec. 9, 2016. 28 pages.
Restriction Requirement for U.S. Appl. No. 14/116,996, filed Dec. 18, 2013 on behalf of Giovanni Mogna, dated Feb. 4, 2015. 11 pages.
Non-Final Office Action for U.S. Appl. No. 14/116,996, filed Dec. 18, 2013 on behalf of Giovanni Mogna, dated May 21, 2015. 29 pages.
Final Office Action for U.S. Appl. No. 14/116,996, filed Dec. 18, 2013 on behalf of Giovanni Mogna, dated Mar. 7, 2016. 22 pages.
Non-Final Office Action for U.S. Appl. No. 14/116,996, filed Dec. 18, 2013 on behalf of Giovanni Mogna, dated Mar. 7, 2016. 22 pages.
Restriction Requirement for U.S. Appl. No. 14/344,047, filed Jul. 28, 2013 on behalf of Giovanni Mogna, dated Feb. 19, 2016. 8 pages.
Non-Final Office Action for U.S. Appl. No. 14/344,047, filed Jul. 28, 2013 on behalf of Giovanni Mogna, dated Oct. 13, 2016. 27 pages.
Restriction Requirement for U.S. Appl. No. 14/344,021, filed May 9, 2014 on behalf of Giovanni Mogna, dated Aug. 14, 2015. 7 pages.
Non-Final Office Action for U.S. Appl. No. 14/344,021, filed May 9, 2014 on behalf of Giovanni Mogna, dated Mar. 18, 2016. 29 pages.
Final Office Action for U.S. Appl. No. 14/344,021, filed May 9, 2014 on behalf of Giovanni Mogna, dated Jan. 31, 2017. 19 pages.
Restriction Requirement for U.S. Appl. No. 14/891,321, filed Nov. 13, 2015 on behalf of Giovanni Mogna, dated Nov. 16, 2016. 8 pages.
Non-Final Office Action for U.S. Appl. No. 14/891,321, filed Nov. 13, 2015 on behalf of Giovanni Mogna, dated Apr. 19, 2017. 14 pages.
Office Action Inquiry for Russian Patent Application No. 2015148750/15(075025) filed May 14, 2014 on behalf of Probiotical S.P.A. dated Mar. 5, 2018. 14 pages. (Russian Original + English Translation).
Patent Search Report for Russian Patent Application No. 2015148750/15(075025) filed May 14, 2014 on behalf of Probiotical S.P.A. dated Mar. 5, 2018. 4 pages. (Russian Original + English Translation).
Japanese Patent Office Official Office Action for Japanese Patent Application No. 2016-513453, dated Jan. 9, 2018. 9 pages. (English Translation + Japanese Original).
Chinese Patent Office First Office Action for Chinese Patent Application No. 201480027970.9, dated Jul. 3, 2018. 12 pages (Chinese Original + English translation).
Chinese Search Report for Chinese Application No. 201480027970.9 filed May 14, 2014 on behalf of Probiotical S.P.A. dated Jun. 21, 2018, 7 pages. (Chinese Original + English Translation).
Peng F., et al., "Health Education for Kidney Diseases," Hubei Science & Technology Press, Dec. 31, 2007, p. 102 (Chinese Original + English Translation).
"Study on Optimization of Exopolysaccharide and Characteristics of *Streptococcus thermophilus* ST1," 2011. 73 pages (7-8). (English Abstract Only).
Wang Q., et al., "Urinary Tract Infections," Shanghai Liandong Press, Jul. 31, 2001, p. 4.
7th Probiotics, Prebiotics & New Foods Proceedings and Abstracts URL: http://www.probioticsprebiotics-newfood.com/pdf/7th_Probiotics_Prebiotics_Newfood.pdf> pp. 1-206, Sep. 2013.

"7th Probiotics & Prebiotics—new food", Universita Urbaniana, Rome. Poster 66: "Effectiveness of the Two Microorganisms *L. fermentum* LF15 and *L. plantarum* LP01, Formulated in Slow Release Vaginal Tablets, in Women Affected by Bacterial Vaginosis (BvV): A Pilot Study", pp. Cover-50, Jul. 2013.
Anukam et al., "Lactobacillus plantarum and Lactobacillus fermentum with Probiotic Potentials Isolated from the Vagina of Healthy Nigerian Women", Research Journal of Microbiology 2(1): pp. 81-87, 2007, 8 pages. <academicjournals.com>.
Champagne, et al: "The determination of viable counts in probiotic cultures microencapsulated by spray-coating", Food 7Microbiology, Academic Press Ltd, London, GB, vol. 27, No. 8, Dec. 1, 2010 (Dec. 1, 2010), pp. 1104-1111. Abstract Only, 1 page.
Douillard et al. "Comparative Genomic and Functional Analysis of 100 Lactobacillus rhamnosus Strains and Their Comparison with Strain GG" PLOS Genetics, Aug. 2013, vol. 9, No. 8, 15 pages.
Gurbuz et al. "Effect of N-Acetyl Cysteine on Helicobacter pylori" Southern Medical Journal; Nov. 2005; vol. 98; No. 11, pp. 1095-1097, 4 pages.
Mathews, H.M.L. et al., "Sodium Bicarbonate as a Single Dose Antacid in Obstetric Anaesthesia", Anaesthesia, vol. 44, pp. 590-591, (1989).
Mogna, L. et al., "Screening of Different Probiotic Strains for Their In Vitro Ability to Metabolise Oxalates—Any Prospective Use in Humans?", J Clin. Gastroenterol, vol. 48, Suppl.1, S91-S95, (2014), 5 pages.
Scardovi, V. et al., "Multiple Electrophoretic Forms of Transaldolase and 6- Phosphogluconic Dehydrogenase and Their Relationships to the Taxonomy and Ecology of the Bifidobacteria", Intl Journal of Systematic Bacteriology, vol. 29, No. 4, pp. 312-327, (1979), 16 pages.
Ventura, M. et al., "Identification and Tracing of *Bifidobacterium* Species by Use of Enterobacterial Repetitive Intergenic Consensus Sequences", Applied and Environmental Microbiology, vol. 69, No. 7, pp. 4296-4301, (Jul. 2003), 6 pages.
Wikipedia "Colony-forming unit" Downloaded from the internet Apr. 13, 2017. http://en.wikipedia.org/wiki/Colony-forming_unit. 1 page.
Wiktionary "Cluster—definition" retrieved from the internet on Apr. 27, 2017 from http://web.archive.org/web/20100214060846/https://en.wiktionary.org/wiki/cluster. 4 pages.
Ying, et al: "Microencapsulated Lactobacillus rhamnosus GG Powders: Relationship of Powder Physical Properties to Probiotic Survival during Storage", Journal of Food Science, vol. 75, No. 9, Nov. 1, 2010, pp. E588-E595, 8 pages.
Zarate, G. et al., "Protective Effect of Vaginal Lactobacillus Paracasei CRL 1289 Against Urogenital Infection Produced by *Staphylococcus aureus* in a Mouse Animal Model", Infectious Diseases in Obstetrics and Gynecology, vol. 2007, 6 pages.
First Examination Report dated Feb. 12, 2016 for Chilean application No. 2013002148 filed on Jul. 26, 2013, 21 pages.
Office Action for Japanese Patent Application No. JP2016513455, dated Jan. 16, 2018, 7 pages (English Translation+ Japanese Original).
Non-Final Office Action for U.S. Appl. No. 13/982,255, filed Mar. 10, 2015 on behalf of Probiotical S.P.A. dated Mar. 10, 2015, 10 pages.
Non-Final Office Action for U.S. Appl. No. 15/265,706, filed Sep. 14, 2016 on behalf of Probiotical S.P.A. dated Jul. 11, 2017, 13 pages.
Final Office Action for U.S. Appl. No. 15/265,706, filed Sep. 14, 2016 on behalf of Probiotical S.P.A. dated Feb. 2, 2018. 18 pages.
Non-Final Office Action for U.S. Appl. No. 14/113,211, filed Nov. 26, 2013 on behalf of Probiotical S.P.A. dated Dec. 7, 2017. 19 pages.
Notice of Allowance for U.S. Appl. No. 14/117,003, filed Dec. 27, 2013 on behalf of Probiotical S.P.A. dated Nov. 22, 2016, 8 pages.
Notice of Allowance for U.S. Appl. No. 14/117,003, filed Dec. 27, 2013 on behalf of Probiotical S.P.A. dated Jul. 6, 2017, 6 pages.
Non-Final Office Action for U.S. Appl. No. 14/116,999, filed Dec. 20, 2013 on behalf of Probiotical S.P.A. dated Jan. 5, 2018. 18 pages.

(56) References Cited

OTHER PUBLICATIONS

Non-Final Office Action for U.S. Appl. No. 14/116,996, filed Dec. 18, 2013 on behalf of Probiotical S.P.A. dated Mar. 27, 2017, 16 pages.
Final Office Action for U.S. Appl. No. 14/116,996, filed Dec. 18, 2013 on behalf of Probiotical S.P.A. dated Dec. 14, 2017. 17 pages.
Final Office Action for U.S. Appl. No. 14/344,047, filed Jul. 28, 2014 on behalf of Probiotical S.PA. dated Aug. 4, 2017, 29 pages.
Non-Final Office Action for U.S. Appl. No. 14/344,021, filed May 9, 2014 on behalf of Probiotical S.PA. dated Jul. 24, 2017, 13 pages.
Notice of Allowance for U.S. Appl. No. 14/344,021, filed May 9, 2014 on behalf of Probiotical S.P.A. dated Dec. 15, 2017. 7 pages.
Notice of Allowance for U.S. Appl. No. 14/344,021, filed May 9, 2014 on behalf of Probiotical S.PA. dated Mar. 27, 2018. 7 pages.
Final Office Action for U.S. Appl. No. 14/346,941, filed Mar. 24, 2014 on behalf of Probiotical S.PA. dated Jan. 22, 2018. 14 pages.
Restriction Requirement for U.S. Appl. No. 14/891,321, filed Nov. 13, 2015 on behalf of Probiotical SP.A. dated Jun. 16, 2017, 5 pages.
Final Office Action for U.S. Appl. No. 14/891,321, filed Nov. 13, 2015 on behalf of Probiotical S.P.A. dated Apr. 25, 2018. 8 pages.
Non-Final Office Action for U.S. Appl. No. 14/891,321, filed Nov. 13, 2015 on behalf of Probiotical S.PA. dated Sep. 6, 2017, 11 pages.
Office Action for Russian Patent Application No. 2013148474/10(075409) filed May 9, 2012 on behalf of Probiotical S.P.A. dated May 19, 2017. 11 pages. (Russian Original + English Translation).
Office Action for Russian Patent Application No. 2013148476/15 filed May 9, 2012 on behalf of Probiotical S.P.A. dated May 31, 2017. 15 pages. (Russian Original + English Translation).
Office Action for Russian Patent Application No. 2014110640/05(016714) filed Sep. 21, 2012 on behalf of Probiotical S.P.A. dated Sep. 2, 2016. 9 pages. (Russian Original + English Translation).
Notice of Allowance for U.S. Appl. No. 14/116,999, filed Dec. 20, 2013 on behalf of Probiotical S.P.A. dated Sep. 4, 2018. 9 pages.
Wiktionary "Bifidogenic" Last modified Jul. 19, 2014, Downloaded from the internet Apr. 13, 2017. http://en.wiktionary.org/wiki/bifidogenic. 1 page.
"The Language of Prevention" from National Public Health Partnership, 2006. Melbourne: NPHP. 9 pages.
Advisory Action U.S. Appl. No. 14/344,047, filed Jul. 28, 2014 on behalf of Giovanni Mogna, dated Nov. 28, 2017. 13 pages.
An excerpt of the text book "Basic microbiology" (Wesley A. Volk and Jay C. Brown. 8th Edition, 1997) (5 pages).
Bondarenko V. M. Molecular-cellular mechanisms of therapeutic action of probiotics. Biologicals. Prevention, diagnosis, treatment. Scientific center of expertise of medical application of the Ministry of health of the Russian Federation (Moscow) 2010 No. 1 (37) p. 31-34; 6 pages.
Botes, M., et al. "Evaluation of Enterococcus mundtii ST4SA and Lactobacillus plantarum 423 as probiotics by using a gastrointestinal model with infant milk formulations as substrate", International Journal of Food Microbiology (Dec. 2008), 128(2), 362-370. Abstract Only.
Decision of Rejection for CN201280022854 filed on behalf of Probiotical S.P.A. on Nov. 11, 2013, dated Sep. 8, 2017. (Chinese Original + English translation). 18 pages.
Decision to Grant dated May 23, 2017 for Russian Patent Application No. 2014107771/10 filed on Sep. 10, 2012 on behalf of Probiotical S.P.A, 2 pages. (Russian Original + 2 pages of English Translation).
Final Office Action for U.S. Appl. No. 14/113,211, filed Nov. 26, 2013, on behalf of Hoffmann-Eitle SRL, dated Sep. 28, 2018. 23 pgs.
Final Office Action for U.S. Appl. No. 14/116,996, filed Dec. 18, 2013 on behalf of Probiotical S.P.A. dated Jan. 25, 2019. 29 pages.
Fourth Office Action for Chinese Patent Application No. 201280015994.3 filed on behalf of Probiotical S.P.A. dated May 22, 2018. 20 pages. (English Translation + Chinese Original).
Giglione, E., et al. "The Association of Bifidobacterium breve BR03 and B632 is Effective to Prevent Colics in Bottle-fed Infants", Journal of Clinical Gastroenterology, vol. 50 (2), S164-S167, (Nov. 2016). 4 pages.
International Preliminary Report on Patentability for Application No. PCT/IB2012/001848 filed Sep. 21, 2012 on behalf of Probiotical S.P.A. dated Mar. 25, 2014. 4 pages. (English Only).
International Preliminary Report on Patentability for International Application No. PCT/IB2014/000731 filed May 14, 2014 on behalf of Probiotical S.P.A. dated Nov. 17, 2015. 11 pages.
Jackson, S.A. et al., "Improving End-User Trust in the Quality of Commercial Probiotic Products", Frontiers in Microbiology, Apr. 2019, vol. 10, Article 739, 15 pages. http://www.frontiersin.org.
Japanese Office Action for Japanese Application No. 2014-529082 filed Mar. 7, 2014 on behalf of Probiotical S.P.A. dated Jul. 19, 2016. 13 pages (Japanese Original + English Translation).
Kaewnopparat, S., et al. "In vitro probiotic properties of Lactobacillus fermentum SK5 isolated from vagina of a healthy woman", Anaerobe (Aug. 2013), 22, 6-13. 8 pages.
Klemenak, M., et al., "Administration of Bifidobacterium breve Decreases the Production of TNF-a in Children with Celiac Disease," Dig Dis Sci. 60(11):3386-92, 2015. 7 pages.
Lai, et al., "Lansoprazole for the Prevention of Recurrences of Ulcer Complications From Long-Term Low-Dose Aspirin Use", N Engl J Med. 346 (26) 2002: 2033-2038.
McFarland, et al. "Strain-Specificity and Disease-Specificity of Probiotic Efficacy: A Systematic Review and Meta-Analysis", Frontiers in Medicine, vol. 5, Article 124, (May 2018), 14 pages.
Mogna, et al. "Capability of the Two Microorganisms Bifidobacterium breve B632 and Bifidobacterium breve BR03 to Colonize the Intestinal Microbiota of Children", Journal of Clinical Gastroenterology, vol. 48 (1), S37-S39, (Nov. 2014). 3 pages.
Non-Final Office Action for U.S. Appl. No. 14/113,211, filed Nov. 26, 2013 on behalf of Hoffmann-Eitle SRL, dated May 29, 2019. 29 pages.
Non-Final Office Action for U.S. Appl. No. 15/265,706, filed Sep. 14, 2016 on behalf of Probiotical S.P.A.. dated Apr. 17, 2019. 27 pages.
Non-Final Office Action for U.S. Appl. No. 15/902,977, filed Feb. 22, 2018 on behalf of Hoffmann-Eitle SRL, dated Oct. 31, 2019. 20 pages.
Notice of Allowance for U.S. Appl. No. 14/116,999, filed Dec. 20, 2013, on behalf of Probiotical S.P.A. dated Dec. 26, 2018. 14 pages.
Notice of Allowance for U.S. Appl. No. 14/117,003, dated Nov. 24, 2017, 5 pages.
Notice of Allowance for U.S. Appl. No. 14/346,941, filed Mar. 24, 2014 on behalf of Giovanni Mogna, dated Aug. 6, 2018. 8 pages.
Notice of Allowance for U.S. Appl. No. 14/346,941, filed Mar. 24, 2014 on behalf of Probiotical North America Inc.. dated Apr. 8, 2019. 29 pages.
Notice of Allowance for U.S. Appl. No. 14/116,996, filed Dec. 18, 2013 on behalf of Giovanni Mogna, dated Sep. 24, 2019. 16 pages.
Office Action for Russian Patent Application No. 2015148750/15 filed May 14, 2014 on behalf of Probiotical S.P.A. dated Mar. 5, 2018. 19 pages (Russian Original + English Translation).
Restriction Requirement for U.S. Appl. No. 16/368,655, filed Mar. 28, 2019 on behalf of Probiotical S.P.A. dated Oct. 10, 2019. 7 pages.
Rowe, R.C. et al., "Handbook of Pharmaceutical Excipients", Chemical Industry Press, 4th Edition, pp. 692-693, (Jan. 31, 2005), 9 pages. (English Translation + Chinese Original).
Russian Patent Office Official Action for Russian Patent Application No. 2015148752/15 filed on behalf of Probiotical S.P.A. dated Apr. 24, 2018. 11 pages (Russian original + English translation).
Russian Search Report for Russian Application No. 2015148752/15 filed on May 14, 2014 on behalf of Probiotical S.P.A. dated Apr. 20, 2018. 4 pages. (Russian original + English translation).
Simone, et al. "The Probiotic Bifidobacterium breve B632 Inhibited the Growth of Enterobacteriaceae within Colicky Infant Microbiota Cultures", Hindawi Publishing Corporation, BioMed Research International, vol. 2014, article ID 301053 (Aug. 2014). 7 pages.
Wikipedia definition of p-value (printed on Jul. 3, 2018) 12 pages. http://en.wikipedia.org/wiki/P-value.

(56) References Cited

OTHER PUBLICATIONS

Wikipedia entry for "yeast", dated Mar. 1, 2011 (13 pages).
Examination Report for Indian Application No. 8722/CHENP/2013 filed on behalf of Probiotical S.P.A. dated Jul. 5, 2018. 8 Pages. (Hindi + English Translation).
Hearing Notice for Indian Application No. 8722/CHENP/2013 filed on behalf of Probiotical S.P.A. Date of Dispatch: Oct. 17, 2019. 3 Pages (Hindi+ English Translation).
Preliminary office Action for Brazilian Application No. BR112013028709-8 filed on May 9, 2012 on behalf of Probiotical S.P.A. dated Aug. 13, 2019. 5 Pages (Portuguese and Informal English Translation).
Basic Microbiology, Eighth edition. Wesley Volk and Jay Brown, eds. Addison-Welsey (1997), pp. 221, 344-345, 5 pages.
Bifisterol Class IIA Medical Device for Oral Use Pamphlet/Packaging from http://www.probiotical.com. 2 pages. 2015.
Bifisterol Probiotic Product Pamphlet from http://www.probiotical.com. 2 pages 2015.
Brazilian Office Action for Brazilian Application No. BR112013028946-0 dated Oct. 17, 2019 on behalf of Probiotical S.P.A., 5 pages. Brazilian + English translation.
Brazilian Office Action for Brazilian Application No. BR112013028705-5 dated Aug. 14, 2019 on behalf of Probiotical S.P.A., 6 pages. Brazilian + English translation.
Brazilian Patent Office Official Action for Brazilian Patent Application No. BR112015027536-2 filed on behalf of Probiotical S.P.A. , dated Oct. 2, 2019 , 6 pages. (Brazilian + English translation).
Decision to Grant for Russian Patent Application No. 2014107771/10 filed Sep. 10, 2012 on behalf of Probiotical S.P.A. dated May 23, 2017. 11 pages (Russian original+ Partial English translation).
Final Office Action for U.S. Appl. No. 14/113,211, filed Nov. 26, 2013 on behalf of Giovanni Mogna, dated Mar. 4, 2020. 25 pages.
Japanese Patent Office Decision to Grant for Japanese Patent Application No. 2016-513453 filed on behalf of Probiotical S.P.A , certification date Sep. 3, 2019, dated Sep. 10, 2019, 7 pages (Japanese + English translation).
Non-Final Office Action for U.S. Appl. No. 16/368,655, filed on behalf of Probiotical S.p.A. dated Mar. 2, 2020. 22 pages.
Notice of Allowance for U.S. Appl. No. 14/116,996, filed Dec. 18, 2013 on behalf of Giovanni Mogna, dated Feb. 26, 2020. 10 Pages.
Notification of Reexamination for Chinese Patent Application No. CN201280022854 in the name of Probiotical S.P.A, dated Sep. 29, 2018. (Chinese Original + English Translation). 14 pages.
Notification of Reexamination for Japanese Patent Application No. JP2014509850 in the name of Probiotical S.P.A, dated Feb. 16, 2016. (Japanese Original + English Translation). 5 pages.
Bozzi Cionci, N., et al., "Therapeutic Microbiology: The Role of Bifidobacterium breve as Food Supplement for the Prevention/Treatment of Paediatric Diseases," *Nutrients*, 10, 1723,Published: Nov. 10, 2018. 27 Pages.

Final Office Action for U.S. Appl. No. 16/368,655, filed Mar. 28, 2019 on behalf of Probiotical S.P.A dated Jul. 14, 2020 14 pages.
Notice of Allowance for U.S. Appl. No. 14/116,996, filed Dec. 18, 2013 on behalf of Giovanni Mogna, dated May 6, 2020. 11 Pages.
Notice of Allowance for U.S. Appl. No. 15/902,977, filed Feb. 22, 2018 on behalf of Probiotical S.P.A. dated Apr. 23, 2020. 5 Pages.
Decision of Rejection for Chinese Application No. 201280031991.7, dated May 12, 2020, with English translation. 14 pages.
Notice of Allowance (Technical Examination Report) dated Sep. 14, 2020, published in Brazilian Industrial Property Journal of Sep. 29, 2020 for Brazilian Application No. BR112013028709-8 filed on May 9, 2012 on behalf of Probiotical S.P.A. 5 Pages (Portuguese + partial Eng trans.).
Canadian Office Action for CA Application No. 2,912,013 filed on May 14, 2014 on behalf of Probiotical S.P.A. dated Aug. 24, 2020. 4 pages.
Koren Office Action for KR Application No. 102015035288 filed on May 14, 2014 on behalf of Probiotical S.P.A. dated Aug. 11, 2020 8 pages (English + Original).
Notice of Allowance for U.S. Appl. No. 14/116,996, filed Dec. 18, 2013 on behalf of Giovanni Mogna, dated Aug. 14, 2020. 10 Pages.
Notice of Allowance for U.S. Appl. No. 15/902,977, filed Feb. 22, 2019 on behalf of Giovanni Mogna dated Oct. 13, 2020 17 pages.
Brazilian Office Action for Brazilian Application No. BR112013028496-0 filed May 9, 2012, on behalf of Probiotical S.P.A. dated Oct. 6, 2020. Portuguese Original + English Translation. 12 Pages.
Notice of Allowance for U.S. Appl. No. 14/116,996, filed Dec. 18, 2013 on behalf of Giovanni Mogna, dated Dec. 3, 2020. 11Pages.
Brazilian Office Action for Brazilian Application No. BR112013028705-5 filed on May 9, 2012 on behalf of Probiotical S.P.A., dated Dec. 14, 2020. 6 pages Brazilian + partial English translation.
Corrected Notice of Allowability for U.S. Appl. No. 14/116,996, filed Dec. 18, 2013 on behalf of Giovanni Mogna, dated Mar. 1, 2021. 3 pages.
Notice of Allowance for U.S. Appl. No. 15/902,977, filed Feb. 22, 2018 on behalf of Probiotical S.P.A. dated Jan. 25, 2021. 6 pages.
Patent Certificate for IN Application No. 1949/MUMNP/2013 filed on May 9, 2012 on behalf of Probiotical S.P.A. Grant Date: Feb. 9, 2021 28 pages.
Non-Final Office Action for U.S. Appl. No. 16/368,655, filed Mar. 28, 2019, on behalf of Probiotical S.p.A. dated Apr. 22, 2021, 19 Pages.
Non-Final OfficeAction for U.S. Appl. No. 14/113,211, filed Nov. 26, 2013 onbehalf of Giovanni Mogna. dated Apr. 23, 2021. 26pages.
Shin, J.M. et al."Pharmacology of Proton Pump Inhibitors", Curr Gastroenterol Rep., Dec. 2008,10 (06), pp. 528-534, 11 pages.

* cited by examiner

COMPOSITION COMPRISING LACTIC ACID BACTERIA FOR USE IN THE PREVENTIVE AND/OR CURATIVE TREATMENT OF RECURRENT CYSTITIS

CROSS REFERENCE TO RELATED APPLICATIONS

The present application is the U.S. national stage entry of International Patent Application No. PCT/IB2014/000731, filed internationally on May 14, 2014, which, in turn, claims priority to Italian Patent Application No. MI2013A000793 filed on May 14, 2013.

FIELD

The present invention relates to a composition comprising lactic bacteria for use in the preventive and/or curative treatment of bacterial infections and related inflammations of the urinary tract and/or bladder, in particular for the treatment of recurrent cystitis.

BACKGROUND

Pathogenic bacteria belonging to the species *Escherichia coli* are known to be able to adhere to the epithelial cell surface of the urinary bladder (urothelium). For this and other reasons, it is known that pathogenic bacteria belonging to the species *Escherichia coli* are responsible for more than 80% of the cases of bacterial infections, which cause bladder inflammations (cystitis). Cystitis, in particular recurrent cystitis, causes discomfort and pain, at times even in acute form.

SUMMARY

The present invention describes a composition, supplement product, medical device or a food composition comprising at least one strain of bacteria having both a specific antibacterial activity against *E. coli* and an anti-inflammatory activity with stimulation of the Interleukin IL-4 and Interleukin IL-10 production and at least one strain of bacteria having an oxalate-degrading activity. The composition herein described can be used in the preventive and/or curative treatment of bacterial infections and related inflammations of the urinary tract and/or bladder.

DETAILED DESCRIPTION

Figure 1:
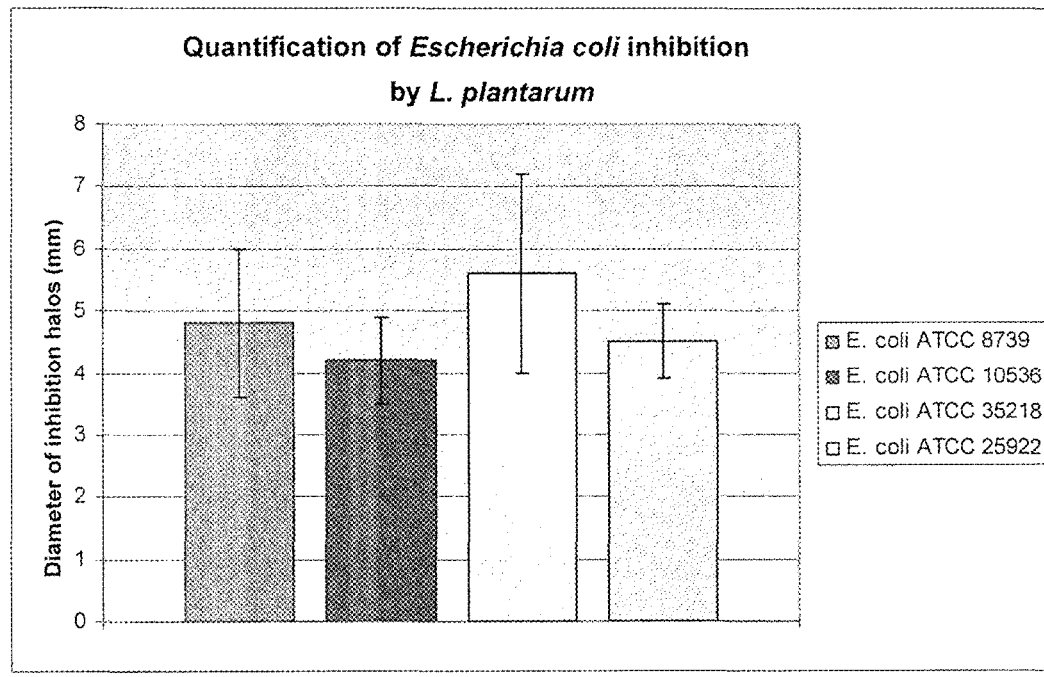
FIG. 1 shows the quantification of *E.coli* (ATCC 8739, ATCC 10536, ATCC 35218, ATCC 25922) inhibition by the strain Lactobacillus plantarum LMG P-21021-LP01.

In view of the above, there is a need to intervene both against bacterial infections caused by *E. coli* and the related inflammations of the urinary tract and/or bladder.

Therefore, there is a need to efficiently intervene against pathogens belonging to the species *Escherichia coli* both through a barrier effect, in order to reduce the adhesion of the pathogen itself to the epithelial cells of the urinary bladder, and through an anti-*E. coli* activity, for hindering the development and proliferation of the pathogen itself. In particular, there is a need to have a treatment for preventing and/or curing cystitis, in particular recurrent cystitis, by adopting a treatment compatible with the physiological habitat and which is well tolerated so that to be administered for a continuous use without side effects. Finally, there is a need to have a natural and effective barrier effect, in the case of both an acute episode and possible relapses, which continues over the time for ensuring a long-term protection and assuring a long-lasting effective preventive and/or curative treatment.

The Applicant, following to an extended and intense research activity, gave a response to the above-cited needs. In fact, the Applicant, after testing and studying many strains of lactic bacteria, succeeded to select only some of them. The selected strains have, at the same time, an activity against the pathogenic bacteria *E. coli* which cause infections and a high anti-inflammatory activity since they are strains of bacteria producing interleukin 4 (IL-4) and interleukin 10 (IL-10).

It is an object of the present invention a composition for use in the preventive and/or curative treatment of bacterial infections and related inflammations of the urinary tract and/or bladder, having the characteristics as disclosed in the appended claim.

Said composition is preferably for use in the preventive and/or curative treatment of cystitis, in particular recurrent cystitis.

By preventive and/or curative treatment is meant to also include circumstances wherein the urinary tract and/or bladder inflammation is limited, reduced or attenuated, which improve the health conditions of the subject being treated.

Preferred embodiments of the present invention are contemplated in the following detailed description.

In the context of the present invention by composition is meant to include a pharmaceutical composition, or a supplement product or a medical device or a food composition.

It is an object of the present invention a composition comprising a mixture of bacteria which comprises or, alternatively, consists of: strains of bacteria having both a specific antibacterial activity against *E. coli* and an anti-inflammatory activity with stimulation of the Interleukin IL-4 and Interleukin IL-10 production, and strains of bacteria having an oxalate-degrading activity.

It is an object of the present invention a composition wherein said mixture comprises or, alternatively, consists of: at least a strain of bacteria having both a specific antibacterial activity against *E. coli* and an anti-inflammatory activity with stimulation of the Interleukin IL-4 and Interleukin IL-10 production, combined with at least a strain of bacteria having an oxalate-degrading activity.

It is an object of the present invention a composition comprising or, alternatively, consisting of a mixture of bacteria which comprises or, alternatively, consists of at least a strain of bacteria selected from the group comprising the strain *Lactobacillus plantarum* LMG P-21021 -LP01 and the strain *Lactobacillus plantarum* LMG P-21020 -LP02, combined with at least a strain of bacteria selected from the group comprising the strain *Lactobacillus paracasei* DSM 24243 -LPC09, the strain *Lactobacillus gasseri* DSM 18299 -LGS01, the strain *Lactobacillus gasseri* DSM 18300 -LGS02, the strain *Lactobacillus acidophilus* DSM 24303 -LA07 and the strain *Lactobacillus acidophilus* DSM 21717 -LA02, for use in the preventive and/or curative treatment of bacterial infections and related inflammations of the urinary tract and/or bladder.

The strain *Lactobacillus plantarum* LMG P-21021 -LP01 was deposited by Mofin Srl Company on 16 Oct. 2001 at the BCCM LMG center.

The strain *Lactobacillus plantarum* LMG P-21020 -LP02 was deposited by Mofin Srl Company on 16 Oct. 2001 at the BCCM LMG center.

The strain *Lactobacillus paracasei* DSM 24243 -LPC09 was deposited by Probiotical S.p.A. Company on 23 Nov. 2010 at the DSMZ center.

The strain *Lactobacillus gasseri* DSM 18299 -LGS01 was deposited by Anidral Srl Company, now Probiotical S.p.A., on 24 May 2006 at the DSMZ center.

The strain *Lactobacillus gasseri* DSM 18300 -LGS02 was deposited by Anidral Srl Company, now Probiotical S.p.A., on 24 May 2006 at the DSMZ center.

The strain *Lactobacillus acidophilus* DSM 24303 -LA07 was deposited by Probiotical S.p.A. Company on 23 Nov. 2010 at the DSMZ center.

The strain *Lactobacillus acidophilus* DSM 21717 -LA02 was deposited by Probiotical S.p.A. Company on 6 Aug. 2008 at the DSMZ center.

In a preferred embodiment, the composition comprises or, alternatively, consists of a mixture of bacteria which comprises or, alternatively, consists of *Lactobacillus plantarum* LMG P-21021 -LP01 combined with at least a strain of bacteria selected from the group comprising the strain *Lactobacillus paracasei* DSM 24243 -LPC09, the strain *Lactobacillus gasseri* DSM 18299 -LGS01, the strain *Lactobacillus gasseri* DSM 18300 -LGS02, the strain *Lactobacillus acidophilus* DSM 24303 -LA07 and the strain *Lactobacillus acidophilus* DSM 21717 -LA02; preferably in a weight ratio comprised from 4:1 to 3:1; even more preferably 1:1. Said compositions are for use in the preventive and/or curative treatment of cystitis, in particular of recurrent cystitis.

In another preferred embodiment, the composition comprises or, alternatively, consists of a mixture of bacteria which comprises or, alternatively, consists of *Lactobacillus plantarum* LMG P-21020 -LP02 combined with at least a strain of bacteria selected from the group comprising the strain *Lactobacillus paracasei* DSM 24243 -LPC09, the strain *Lactobacillus gasseri* DSM 18299 -LGS01, the strain *Lactobacillus gasseri* DSM 18300 -LGS02, the strain *Lactobacillus acidophilus* DSM 24303 -LA07 and the strain *Lactobacillus acidophilus* DSM 21717 -LA02; preferably in a weight ratio comprised from 4:1 to 3:1; even more preferably 1:1, Preferably, said compositions are for use in the preventive and/or curative treatment of cystitis, in particular of recurrent cystitis.

Said compositions can further comprise a cranberry extract, preferably a dry cranberry extract, and/or can further comprise a D-mannose.

In another preferred embodiment, said compositions can comprise, in addition to the strains of bacteria described above and the amounts disclosed above, a cranberry extract, preferably a dry cranberry extract; and/or can comprise a D-mannose; and/or can comprise a plant gum and/or a plant gelatin. The plant gum and/or the plant gelatin is preferably selected from the group comprising a tannate or a gelatin tannate, an alginate, a xyloglucan or xylogel, a guar gum, a tara gum, an acacia, carob, oat, bamboo fiber, citrus fruit fibers and glucomannans. Preferably it is a guar gum. The selected plant gum and/or plant gelatin reduces the bacterial translocation of *E. coli* from the intestine to the bladder.

Preferably, all the above-described compositions can further comprise a fiber with prebiotic activity selected from inulin, fructo-oligosaccharides (FOS), galacto- and trans-galacto-oligosaccharides (GOS and TOS), gluco-oligosaccharides (GOSα), xylo-oligosaccharides, (XOS), chitosan-oligosaccharides (COS), soy-oligosaccharides (SOS), isomalto-oligosaccharides (IMOS), resistant starch, pectins, psyllium, arabino-galactans, gluco-mannans and galacto-mannans.

In a preferred embodiment, the composition of the present invention comprises or, alternatively, consists of:

(i) a mixture of bacteria which comprises or, alternatively, consists of *Lactobacillus plantarum* LMG P-21021 -LP01 and *Lactobacillus paracasei* DSM 24243 -LPC09; preferably in a weight ratio comprised from 4:1 to 3:1; even more preferably 1:1, (ii) a cranberry extract, preferably a dry cranberry extract, a D-mannose and a guar gum; preferably in a weight ratio 1:1:1, and (iii) a fructo-oligosaccharide—FOS; preferably in a weight ratio 5:1 relative to the weight of cranberry extract.

In another preferred embodiment, the composition of the present invention comprises or, alternatively, consists of:

(i) a mixture of bacteria which comprises or, alternatively, consists of *Lactobacillus plantarum* LMG P-21020 -LP02 and *Lactobacillus acidophilus* DSM 21717 -LA02; preferably in a weight ratio comprised from 4:1 to 3:1; even more preferably 1:1, (ii) a cranberry extract, preferably a dry cranberry extract, a D-mannose and a guar gum; preferably in a weight ratio 1:1:1, and (iii) a fructo-oligosaccharide—FOS; preferably in a weight ratio 5:1 relative to the weight of cranberry extract.

The composition of the present invention due to the presence of a cranberry extract, preferably a dry extract (trade name PACran®, a dry extract of US cranberry (Cranberry—*Vaccinium macrocarpon*—extract)) is able to establishing a physical-mechanical hindrance against the *Escherichia coli* adhesion to the epithelial cell surface of the urinary bladder (urothelium).

The activity of said cranberry extract is mediated, in particular, by the proanthocyanidin subfraction with the trimers and tetramers characterized by A-type bonds which compete with the adhesins located on the P-type fimbriae (FimH, mannose-sensitive) which uses *E. coli* for mediating its anchoring to the epithelial cells through specific receptors, thereby hindering in a physical-mechanical manner its adhesion and subsequent bladder colonization.

Advantageously, the strain of bacteria *Lactobacillus plantarum* LMG P-21021 - LP01 and/or the strain of bacteria *Lactobacillus plantarum* LMG P-21020 -LP02, in the presence of the cranberry extract, are able to complement and enhance the physical-mechanical hindrance exerted by the cranberry extract as described above, through a barrier-type action even at intestinal level against *E. coli*. These two strains of bacteria *Lactobacillus plantarum* LMG P-21021 -LP01 and *Lactobacillus plantarum* LMG P-21020 -LP02 have a proven *E. coli* activity and a high anti-inflammatory activity since they produce interleukin 4 (IL-4) and interleukin 10 (IL-10).

Preferably, the strain of bacteria *Lactobacillus plantarum* LMG P-21021 - LP01 and/or the strain of bacteria *Lactobacillus plantarum* LMG P-21020 -LP02 are in an amount comprised from 1 to 3 billions of viable cells/dose, even more preferably from 2 to 2.5 billions of viable cells/dose.

The strains of bacteria of the present invention exert a marked barrier-type action against potential Gram-negative pathogens, with particular reference to the species *Escherichia coli* and a high anti-inflammatory activity since they produce interleukin 4 (IL-4) and interleukin 10 (IL-10).

Advantageously, the strains of bacteria *Lactobacillus paracasei* DSM 24243 -LPC09, *Lactobacillus gasseri* DSM 18299 -LGS01, *Lactobacillus gasseri* DSM 18300 -LGS02, *Lactobacillus acidophilus* DSM 24303 -LA07 and *Lactobacillus acidophilus* DSM 21717 -LA02 are able to carry out a protective action since they exert a barrier effect to the oxalates contained in the cranberry extract, preferably in the form of dry extract. The metabolization of these oxalate molecules prevents the intestinal accumulation and the systemic absorption thereof, thus avoiding the establishment and the maintenance of an inflammatory condition of the intestine, particularly disadvantageous in the occurrence of diverticula.

The strains of bacteria *Lactobacillus paracasei* DSM 24243 -LPC09, *Lactobacillus gasseri* DSM 18299 -LGS01, *Lactobacillus gasseri* DSM 18300 -LGS02, *Lactobacillus acidophilus* DSM 24303 -LA07 and *Lactobacillus acidophilus* DSM 21717 -LA02 metabolize the oxalates and, therefore, have a proved anti-renal gravel activity.

These strains of bacteria prevent the renal accumulation of oxalates thus avoiding the renal gravel formation and, thereby, impeding the establishment and the maintenance of an inflammatory condition of the urinary tract particularly disadvantageous for the health status of a bladder subjected to recurrent cystitis.

The percentage of oxalate degradation is as follows:

*Lactobacillus paracasei* DSM 24243 -LPC09, greater than 68%;

*Lactobacillus gasseri* DSM 18299 -LGS01, greater than 68%;

*Lactobacillus gasseri* DSM 18300 -LGS02, greater than 66%;

*Lactobacillus acidophilus* DSM 24303 -LA07, greater than 54%;

*Lactobacillus acidophilus* DSM 21717 -LA02, greater than 50%.

The presence of strains of bacteria degrading oxalates in the composition of the present invention is also important for the following reason. The cranberry extract contains a fair oxalate amount. A prolonged use of cranberry extract could lead to renal gravel formation, which may force the subject to suspend the use thereof. The use of strains degrading oxalates of the present invention prevents this drawback allowing a prolonged administration of cranberry extract.

Preferably, the strains of bacteria *Lactobacillus paracasei* DSM 24243 -LPC09, *Lactobacillus gasseri* DSM 18299-LGS01, *Lactobacillus gasseri* DSM 18300 -LGS02, *Lactobacillus acidophilus* DSM 24303 -LA07 and *Lactobacillus acidophilus* DSM 21717 -LA02 are in an amount comprised from 0.5 to 2 billions of viable cells/dose, even more preferably from 1 to 1.5 billions of viable cells/dose.

The composition further comprises D-mannose, which enhances the barrier effect exerted by the cranberry extract. In particular, D-mannose in a simple sugar, namely a monosaccharide which, once absorbed in the blood circulation, is neither transformed in glycogen nor exploited by the organism, with a subsequent removal by the kidney and achievement of high concentrations in the urinary tract wherein it will exert its hindering effects against the bacteria being present. In fact, D-mannose has a high affinity for mannose-sensitive lectins, typical proteins of cell membranes of the human organism used by many bacteria for adhering to the urinary mucosae. Additionally, D-mannose also exerts a mechanical action, which inhibits the formation of biofilms that many bacteria are able to produce with the dual purpose of protecting from our immune system elements and from antibiotics, as well as more effectively adhering to the mucosal surface.

The composition of the present invention can further comprise at least a gum, among those described above, which decreases the bacterial translocation of *E. coli* from the intestine to the bladder. The gum can be a plant gum and/or a plant gelatin. The plant gum and/or the plant gelatin is preferably selected from the group comprising a tannate or a gelatin tannate, an alginate, a xyloglucan or xylogel, a guar gum, a tara gum, an acacia, carob, oat, bamboo fiber, citrus fruit fibers and glucomannans. Preferably it is a guar gum. The selected plant gum and/or plant gelatin reduces the bacterial translocation of *E. coli* from the intestine to the bladder. Preferably it is a guar gum. The guar gum exerts a mechanical action at intestinal level, hindering the adhesion of *Escherichia coli* and other pathogens to the mucosa of the organ, thus reducing their translocation through the intestinal wall and the subsequent risk of infection of adjacent organs. In particular, the gum acts by forming a hydrophilic gel, which evenly distributes over the mucosal surface, restoring the physiological barrier effect of this organ, which typically results impaired in the event of intestinal infections by *Escherichia coli* or other pathogens.

In addition, the composition of the present invention further comprises a fiber with prebiotic activity (prebiotic fiber), which can be selected from inulin, fructo-oligosaccharides (FOS), galacto- and trans-galacto-oligosaccharides (GOS and TOS), gluco-oligosaccharides (GOSα), xylo-oligosaccharides, (XOS), chitosan-oligosaccharides (COS), soy-oligosaccharides (SOS), isomalto-oligosaccharides (IMOS), resistant starch, pectins, psyllium, arabino-galactans, gluco-mannans and galacto-mannans. Preferably, it is selected from short chain fructo-oligosaccharides (FOSsc) or galactooligosaccharides GOS which contributes to the growing and replication of the bacterial strains existing in the composition.

The composition of the present invention can further comprise excipients selected from natural flavors, anti-caking agents such as silicon dioxide, black carrot anthocyanins, sucralose.

The mixture of bacteria has a bacterial load comprised from $1\times10^8$ to $1\times10^{12}$ CFU/g of mixture. The composition of the present invention which contains said mixture of bacteria has a bacterial load of about $5\times10^7$-$5\times10^9$ CFU/composition.

It is an object of the present invention a composition comprising a mixture, which comprises or, alternatively, consists of:
(a) a strain of bacterium *Lactobacillus plantarum* LP01 (LMG P-21021) and/or
(b) a strain of bacterium *Lactobacillus paracasei* LPC09 (DSM 24343); said composition further comprises:
(c) a specific muco-adhesive gelling complex, comprised of EPS, exopolysaccharides of bacterial origin (produced by *Streptococcus thermophilus* ST10 DSM 25246 and tara gum, a polysaccharide of plant origin. Said gelling complex is able to establish a mechanical barrier effect throughout the gastro-intestinal tract. Said composition further contains (d) a specific dry extract of US cranberry (Cranberry—PACran®) and (e) a suitable amount of D-mannose (composition).

Due to the presence of cranberry and D-mannose the composition is able to establishing a hindering action of physical-mechanical type against the adhesion of *Escherichia coli* to the epithelial cell surface of the urinary bladder, responsible for most of the cases of bacterial infections which cause inflammations of this organ (cystitis).

Due to the presence of the specific ingredient PACran®, a dry extract of US cranberry (Cranberry, *Vaccinium macrocarpon*), the composition is able to establish a natural physical-mechanical hindrance against the adhesion of *Escherichia coli* to the epithelial cell surface of bladder and urinary tract. Its main activity is related to the proanthocyanidin subfraction (phytochemical component of fruits) containing trace elements which compete with the adhesins located on the P-type fimbriae (Fim H, mannose-sensitive) which uses *E. coli* for mediating its anchoring to the epithelial cells, thereby hindering in a physical-mechanical manner its adhesion and subsequent colonization of urinary tract and bladder.

Such a barrier is further enhanced due to the present of D-mannose, a simple sugar. UPEC bacteria, by binding the D-mannose molecules through the P-type fimbriae, remain in free form in the urine and, thus, are more easily removed by urination. Finally, D-mannose exerts a mechanical action inhibiting the formation of biofilms that many bacteria are able to produce. After exerting its hindering effect, D-mannose is able to bind the cells of the bladder mucosa (of which is constitutive part) restoring a protective layer similar to the physiological one comprised of glycosaminoglycans, which is usually damaged by recurrent inflammations.

The composition further comprises a suitable amount of tara gum which, due to its gelling and muco-adhesive properties, is capable to form a hydrogel within few minutes after ingestion, by virtue of its thixotropic characteristics, thereby creating, in the first part of the gastrointestinal tract a mechanical barrier action against the adhesion of *Escherichia coli* and other pathogens to the mucosa of the organ, thus reducing the translocation thereof through the intestinal wall and the subsequent risk of infection of adjacent organs, among which mainly the bladder. Such a barrier effect is completed and extended throughout the gastro-intestinal tract by the presence of exopolysaccharides (EPS), produced in situ by the microorganism *Streptococcus thermophilus* ST10, which thereby enhance the viscosity of the surrounding environment through a self-regulated, and exclusively mechanical mechanism. The ingestion of the above cited bacterium carries in the human intestine a source of molecules with gelling activity, thus exerting an action totally complementary to that of tara gum.

The above-cited muco-adhesive gelling complex has an innovative property which has to be taken into account: tara gum, like all the gums of plant origin, is progressively degraded by the resident microbiota during its intestinal transit, thereby progressively reducing its gelling power of mechanical hindrance. The gradual reduction of the plant gum action is effectively counterbalanced by the gradual increase of exopolysaccharide (EPS) release in the intestinal lumen by the bacterial strain ST10, which exerts its property mainly in ileum and colon. The synergistic combination of tara gum and exopolysaccharides (EPS) thereby ensures the presence of gelling molecules throughout the gastro-intestinal tract, maximizing and optimizing the mechanical barrier action of the product. The presence, production and retention of the hydrophilic gel in the lumen of the organ can, therefore, be considered for the first time really complete, with a first area wherein the plant gum action is maximum and a second area wherein the exopolysaccharide (EPS) action is maximum.

The two microorganisms *Lactobacillus plantarum* LP01 (LMG P-21021) (for example 2.5 billions/daily dose) and *Lactobacillus paracasei* LPC09 (DSM 24343) (for example 1 billion/daily dose), mediate an enhancement of the barrier effect established by the muco-adhesive gelling complex comprised of tara gum and exopolysaccharides (EPS), by a barrier-type action against *E. coli* even at intestinal level. The Applicant carried out a selection of microorganisms with a marked barrier-type action against potential Gram-negative pathogens, with particular reference to the species *Escherichia coli*, the main role of which in cystitis has been well demonstrated. In addition to the 4 strains of *E. coli* deriving from the ATCC Collection, the barrier action was also quantified against the enterohemorrhagic serotype O157:H7, capable to produce one or more Shiga, and *Klebsiella* spp., toxins, alone or combined with *E. coli*. Following to this research activity, the above-cited strain *Lactobacillus plantarum* LP01 was positively selected, which is able to establish a barrier-type action against both *E. coli* and *Klebsiella*. Furthermore, the microorganism *Lactobacillus paracasei* LPC09 is capable to create a barrier effect to oxalates, ensuring the complete tolerability of the Cranberry extract even in subjects particularly sensitive to small concentrations of these potential inflammatory agents of the intestinal and urinary mucosae.

Thus, it can be concluded that the composition primarily acts by establishing a physical-mechanical hindrance capable to reduce the urothelium adhesion of *Escherichia coli*, which is the main cause of bladder infections and inflammations (cystitis). Furthermore, the presence of the specific muco-adhesive gelling complex comprised of tara gum and exopolysaccharides (EPS) produced in situ by *S. thermophilus* ST10, as well as of the two microorganisms *L. plantarum* LP01 and *L. paracasei* LPC09, mediates an enhancement of the physical-mechanical hindrance mediated by combining Cranberry and D-mannose, with a barrier-type action even at intestinal level against *E. coli* and of the possible translocation of pathogenic microorganisms through the intestinal wall.

Urinary tract infections (UTI) are known to be the most common bacterial infection in women. Most of the UTI are uncomplicated acute cystitis caused by *Escherichia coli* (86%). The present in vivo study carried out by the Applicant was conducted for assessing the efficacy of a composition comprising a dry cranberry extract, D-mannose, a gelling complex comprised of exopolysaccharides (EPS) produced by *Streptococcus thermophilus ST*10 (DSM 25246) and tara gum, as well as the two microorganisms *Lactobacillus plantarum* LP01 (LMG P-21021) and *Lactobacillus paracasei* LPC09 (DSM 24243) in women with uncomplicated acute cystitis.

The following composition was tested: $2.5 \times 10^9$ of viable cells of the strain of bacterium *Lactobacillus plantarum* LMG P-21021 (LP01), $1 \times 10^9$ of viable cells of the strain of bacterium *Lactobacillus paracasei* DSM 24243 (LPC09) and $1 \times 10^9$ of viable cells of the strain of bacterium *S. thermophilus* DSM 25246 (ST10) along with 250 mg of tara gum, 500 mg of a Cranberry extract PACs (Naturex SA, Avignon, France) and 250 mg of D-mannose (Hebei Huaxu Pharmaceutical Co., Shijiazhuang, China).

Methods. 33 premenopausal and non-pregnant women diagnosed with uncomplicated acute cystitis were enrolled in a prospective pilot study and completed the treatment protocol. The subjects were instructed to take two doses per day for the first month, than to continue with 1 sachet per day until the sixtieth day. Nitrites and leukocyte esterase through assessment with urine-reactive stick were used as markers of cystitis, with an analysis carried out at the beginning, after 30 and 60 days, and after one month of follow-up. The typical symptoms of UTI, namely dysuria, frequent emptying of small volumes, urinary urgency, suprapubic pain and macroscopic haematuria were scored 0-3 and assessed during each medical examination.

Results. Positive results for the presence of nitrites and leukocyte esterase were respectively detected in 14 and 20 subjects after 30 days and in 9 and 14 women after 60 days ($p<0.001$). At the end of the follow-up period, positive results for nitrites and leukocyte esterase were recorded only in 4 and 3 of the 24 and 19 subjects (respectively 16.7%, $p=0.103$; 15.8%, $p=0.325$) with negative results after 60 days. The typical symptoms of cystitis, specifically, dysuria, frequent emptying, urgency and suprapubic pain were also significantly ameliorated. No significant differences were recorded for the incidence and severity of haematuria in any medical examination. The present study substantiates the efficacy of the tested composition based on cranberry, D-mannose, an innovative gelling complex and the two microorganisms in significantly ameliorating the annoying symptoms reported by women with acute cystitis.

The present pilot study demonstrates the long-term ability of a combination of dry cranberry extract, D-mannose, a gelling complex comprised of exopolysaccharides (EPS) produced by *S. thermophilus* ST10 and tara gum as well as the two microorganisms *L. plantarum* LP01 and *L. paracasei* LPC09, to significantly ameliorate the annoying symptoms reported by women with acute cystitis. To our knowledge, this is the first study which assesses the efficacy of a combination of lactobacilli with a dry cranberry extract in women with uncomplicated acute cystitis. A relatively low number of relapses was recorded during the first month of follow-up according to the considered parameters, thus suggesting the long-term barrier effect exerted by the product. The acceptance and global tolerability profile were very good, since only two exclusions were recorded during the first and second months of treatment due to a deviation from the protocol and no significant negative events occurred. Cranberry (*Vaccinium macrocarpon* extract) and D-mannose have both an efficacy in hindering, also mechanically, the adhesion of strains of *E. coli* to the urothelium, the epithelium lining most of the urinary tract. This test can represent a natural tool intended for progressively reducing the severity of a cystitis, thus contributing in alleviating the related symptoms. In any case, cranberries have a relatively high content of oxalic acid, a substance which should be avoided by individuals with a tendency to form calcium oxalate renal stones. The strain *L. paracasei* LPC09 is effectively able to metabolize oxalates in vitro, thus providing a potential protection against the risk of intestinal inflammation deriving from a prolonged supplementation with a dry cranberry extract. The gelling complex comprising tara gum and *S. thermophilus* ST10 is able to prolong the mechanical barrier effect usually ensured by the gum throughout the intestine, thus protecting the organism against a possible onset or maintenance of a low-level chronic inflammatory condition.

In the present study, a test with a urine-reactive stick was used together with the assessment of the symptoms for diagnosing UTI and quantifying the efficacy of the tested composition. The convenience and inexpensiveness of the assessment with a urine-reactive stick, allowed it to be a common diagnostic tool, and represents a suitable option to urine analysis and urine microscopy for diagnosing uncomplicated acute cystitis. Furthermore, it is known that the combination of the positive results obtained with reactive stick, in particular nitrite test, with the symptoms, increases the post-test probability of UTI. In particular, the presence of nitrites and leukocyte esterase in urine samples were considered as prominent factors for confirming (both positive) and excluding (both negative) an UTI. In fact, a reactive stick positive for leukocyte esterase or nitrite and negative for the other one, provides a non-definitive diagnostic information and in these patients is thus needed a further assessment. Usually, no nitrite is detectable in the urine. Many enteric Gram-negative bacteria such as coliforms are able to synthetizing nitrite, thereby allowing the detection of their presence by means of a simple test. On the other hand, a leukocyte increase indicates pyuria and it is detected in almost all the renal and urinary tract diseases. Leukocyte esterase is a reliable marker for leukocytes in the urine. Urine cultures are recommended only for patients with suspected acute pyelonephritis, patients with symptoms without resolution or with relapse within from two to four weeks after the completion of the treatment and patients with atypical symptoms.

A simultaneous reduction of the incidence of positive results for nitrites and leukocyte esterase and the severity of the UTI symptoms was recorded, with particular reference to dysuria, frequent emptying, urgency and suprapubic pain. It has to be noted that haematuria maintained almost unchanged throughout the study, probably because a longer period is required for obtaining the urothelium healing and becoming clinically obvious.

In any case, the results obtained from the present study are positive and encouraging.

Example of composition No. 1 (dose 2325 mg) in sachet granules:
Ingredients
Cranberry extract (Cranberry PACran®) 250 mg/dose
D-Mannose 250 mg
*Lactobacillus plantarum* LP01 (LMG P-21021) 125 mg ($2.5 \times 10^9$ CFU/dose)
*Lactobacillus paracasei* LPC09 (DSM 24243) 50 mg ($1 \times 10^9$ CFU/dose)
Short chain fructo-oligosaccharides—FOSsc 1250 mg/dose
Excipients (400 mg/dose)
Natural flavor cranberry; anti-caking agent: silicon dioxide; black carrot anthocyanins; sucralose.

Example of composition No. 2 (dose 2575 mg) in sachet granules:
Ingredients
Cranberry extract (Cranberry PACran®) 250 mg/dose
D-Mannose 250 mg
*Lactobacillus plantarum* LP01 (LMG P-21021) 125 mg ($2.5 \times 10^9$ CFU/dose)
*Lactobacillus paracasei* LPC09 (DSM 24243) 50 mg ($1 \times 10^9$ CFU/dose)
Short chain fructo-oligosaccharides—FOSsc 1250 mg/dose
guar gum 250 mg/dose
Excipients (400 mg/dose)
Natural flavor cranberry; anti-caking agent: silicon dioxide; black carrot anthocyanins; sucralose.

Example of composition No. 3 (dose 2575 mg) in sachet granules:
Ingredients
Cranberry extract (Cranberry PACran®) 500 mg/dose
D-Mannose 250 mg
*Lactobacillus plantarum* LP01 (LMG P-21021) 125 mg ($2.5 \times 10^9$ CFU/dose)
*Lactobacillus paracasei* LPC09 (DSM 24243) 50 mg ($1 \times 10^9$ CFU/dose)
Short chain fructo-oligosaccharides—FOSsc 1250 mg/dose Excipients (400 mg/dose)

Natural flavor cranberry; anti-caking agent: silicon dioxide; black carrot anthocyanins; sucralose.

Example of composition No. 4 (dose 2825 mg) in sachet granules:

Ingredients

Cranberry extract (Cranberry PACran®) 500 mg/dose

D-Mannose 250 mg

*Lactobacillus plantarum* LP01 (LMG P-21021) 125 mg ($2.5 \times 10^9$ CFU/dose)

*Lactobacillus paracasei* LPC09 (DSM 24243) 50 mg ($1 \times 10^9$ CFU/dose)

Short chain fructo-oligosaccharides—FOSsc 1250 mg/dose guar gum 250 mg/dose

Excipients (400 mg/dose)

Natural flavor cranberry; anti-caking agent: silicon dioxide; black carrot anthocyanins; sucralose.

Examples of composition (5-8) correspond to compositions (1-4) wherein the strain of bacteria *Lactobacillus plantarum* LP01 (LMG P-21021) is replaced by the strain of bacteria *Lactobacillus plantarum* LP02 (LMG P-21020) and the strain of bacteria *Lactobacillus paracasei* LPC09 (DSM 24243) is replaced by the strain of bacteria *Lactobacillus acidophilus* DSM 21717 -LA02.

The composition of the present invention can be in solid form, for oral use, as tablet, capsule, granules or powder.

The compositions the present invention, for example in the form of granules for oral use in sachet, have a shelf-life of at least $3.5 \times 10^9$ viable cells at 24 months and at 25° C. It is recommended to take 2 sachets per day during the first 4 weeks, than to continue, for maintenance purposes, with 1 sachet per day over even long periods. The compositions of the present invention are well tolerated by the organism and thus allow a continuous and prolonged use over the time without side effects.

Cytokines with Immunoregulatory Action

This study assessed the induction of cytokines IL-4 and IL-10, which represent the main cytokines with immunoregulatory action. As can be seen in figure A, the tested strains of bacteria *Lactobacillus plantarum* LMG P-21021 -LP01 and *Lactobacillus plantarum* LMG P-21020 -LP02 are able to inducing a statistically significant growth relative to the basal conditions in both the cytokines.

FIG. 1 relates to the quantification of *E.coli* (ATCC 8739, ATCC 10536, ATCC 35218, ATCC 25922) inhibition by the strain Lactobacillus plantarum LMG P-21021-LP01.

Figure 2:
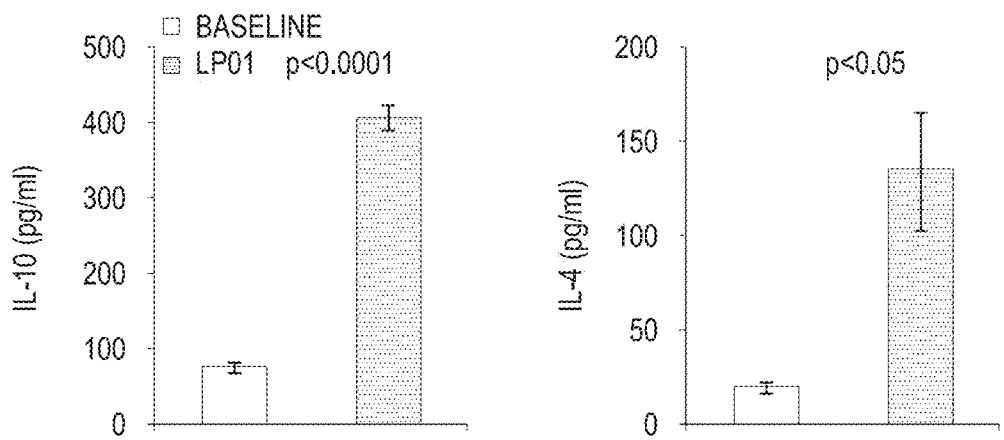
FIG. 2 shows cytokine profile of ten independent experiments.

FIG. 2 shows cytokine profile. Mean±S.E.M. of 10 independent experiments. The statistical meaning is calculated by using the Student's t-test. When it is calculated relative to the basal conditions (non-stimulated PBMC), the values $p<0.05$ are considered statistically significant. The IL-10 production was assessed in the culture supernatant after one day from stimulation. The IL-4 production was assessed in the culture supernatant after five days of stimulation. Similar results were obtained with the strain *Lactobacil/us plantarum* LMG P-21020 -LP02.

Figure 3:
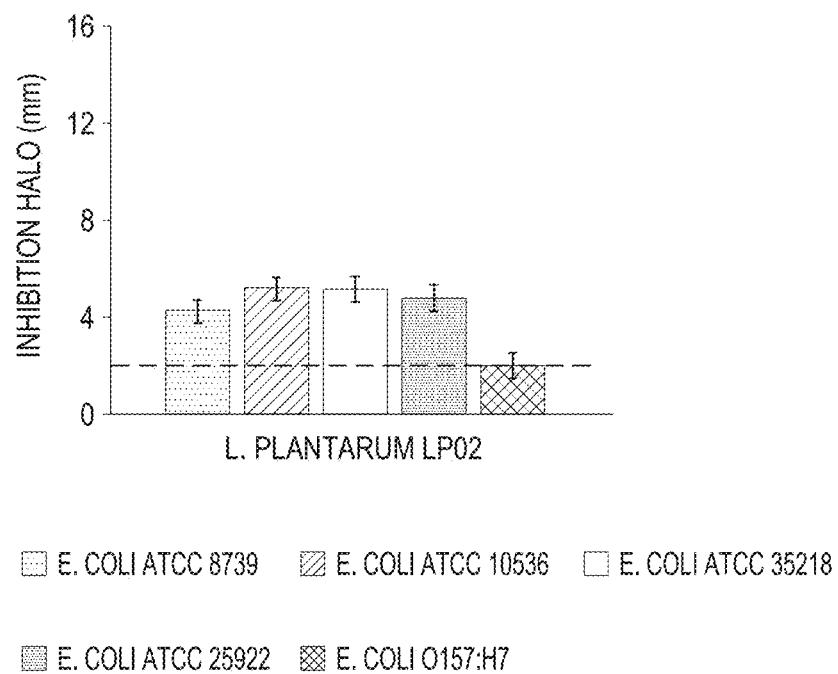
FIG. 3 shows the quantification of *E.coli* (ATCC 8739, ATCC 10536, ATCC 35218, ATCC 25922) inhibition by the strain *Lactobacillus plantarum* LMG P-21020-LP02.

FIG. 3 relates to the quantification of *E.coli* (ATCC 8739, ATCC 10536, ATCC 35218, ATCC 25922) inhibition by the strain *Lactobacillus plantarum* LMG P -21020-LP02.

The invention claimed is:

1. A method to treat bacterial infections caused by *E. coli* and/or related inflammations of the urinary tract and/or bladder in a subject, the method comprising:
    administering to the subject an effective amount of a composition comprising
    a mixture of bacteria, which comprises:
        at least a strain of bacteria selected from the group consisting of the strain *Lactobacillus plantarum* LMG P-21021 (LP01) and the strain *Lactobacillus plantarum* LMG P-21020 (LP02); and
        the strain *Lactobacillus paracasei* DSM 24243 (LPC09);
    a cranberry extract; and
    D-mannose.

2. The method according to claim 1, wherein said mixture of bacteria comprises *Lactobacillus plantarum* LMG P-21021 (LP01), *Lactobacillus paracasei* DSM 24243 (LPC09), and at least a strain of bacteria selected from *Lactobacillus gasseri* DSM 18299 (LGS01), *Lactobacillus gasseri* DSM 18300 (LGS02), *Lactobacillus acidophilus* DSM 24303 (LA07) and *Lactobacillus acidophilus* DSM 21717 (LA02).

3. The method according to claim 1, wherein said mixture of bacteria comprises *Lactobacillus plantarum* LMG P-21020 (LP02), *Lactobacillus paracasei* DSM 24243 (LPC09), and at least a strain of bacteria selected from *Lactobacillus gasseri* DSM 18299 (LGS01), *Lactobacillus gasseri* DSM 18300 (LGS02), *Lactobacillus acidophilus* DSM 24303 (LA07) and *Lactobacillus acidophilus* DSM 21717 (LA02).

4. The method according to claim 1, wherein the infection and/or inflammation is cystitis.

5. The method according to claim 4, wherein the cystitis is recurrent cystitis or uncomplicated acute cystitis.

6. The method according to claim 1, wherein said composition further comprises a plant gum and/or a gelatin.

7. The method according to claim 1, wherein said composition further comprises a fiber with prebiotic activity selected from inulin, fructo-oligosaccharides (FOS), galacto- and trans-galacto-oligosaccharides (GOS and TOS), gluco-oligosaccharides (GOSα), xylo-oligosaccharides, (XOS), chitosan-oligosaccharides (COS), soy-oligosaccharides (SOS), isomalto-oligosaccharides (IMOS), resistant starch, pectins, psyllium, arabino-galactans, glucomannans and galacto-mannans.

8. The method according to claim 1, wherein said composition comprises:
    (i) the mixture of bacteria which comprises *Lactobacillus plantarum* LMG P-21021 (LP01) and *Lactobacillus paracasei* DSM 24243 (LPC09),
    (ii) a cranberry extract, a D-mannose and a guar gum, and
    (iii) a fructo-oligosaccharide —FOS.

9. The method according to claim 1, wherein said composition comprises:
    (i) a mixture of bacteria which comprises *Lactobacillus plantarum* LMG P-21020 (LP02), *Lactobacillus paracasei* DSM 24243 (LPC09), and *Lactobacillus acidophilus* DSM 21717 (LA02),
    (ii) a cranberry extract, a D-mannose and a guar gum, and
    (iii) a fructo-oligosaccharide—FOS.

10. The method according to claim 1, wherein said composition comprises the mixture comprising:
    a strain of bacterium *Lactobacillus plantarum* LP01 (LMG P-21021);
    a strain of bacterium *Lactobacillus paracasei* LPC09 (DSM 24243);
    a fiber with prebiotic activity and tara gum; and
    a dry extract of US cranberry; and
    an amount of D-mannose.

11. The method according to claim 2, wherein the *Lactobacillus plantarum* LMG P-21021 (LP01) and *Lactobacillus paracasei* DSM 24243 (LPC09) are in a weight ratio from 4:1 to 3:1.

12. The method according to claim 2, wherein the *Lactobacillus plantarum* LMG P-21021 (LP01) and *Lactobacillus paracasei* DSM 24243 (LPC09) are in weight ratio 1:1.

13. The method according to claim 3, wherein *Lactobacillus plantarum* LMG P-21020 (LP02) and *Lactobacillus paracasei* DSM 24243 (LPC09) are in a weight ratio from 4:1 to 3:1.

14. The method according to claim 3, wherein the *Lactobacillus plantarum* LMG P-21020 (LP02) and *Lactobacillus paracasei* DSM 24243 (LPC09) are in weight ratio 1:1.

15. The method according to claim 1, wherein the cranberry extract is a dry cranberry extract.

16. The method according to claim 6, wherein the plant gum and/or gelatin is selected from a tannate or a gelatin tannate, an alginate, a xyloglucan or xylogel, a guar gum, a tara gum, an acacia, carob, oat, bamboo fiber, citrus fruit fibers and glucomannans.

17. The method according to claim 7, wherein the fiber with prebiotic activity is a FOS.

18. The method according to claim 8, wherein the *Lactobacillus plantarum* LMG P-21021 (LP01) and the *Lactobacillus paracasei* DSM 24243 (LPC09) are in a weight ratio from 4:1 to 3:1, the cranberry extract, the D-mannose and the guar gum are in a weight ratio of 1:1:1, and the FOS and the cranberry extract are in a weight ratio of 5:1.

19. The method according to claim 9, wherein the *Lactobacillus plantarum* LMG P-21020 (LP02) and the *Lactobacillus acidophilus* DSM 21717 (LA02) are in a weight ratio from 4:1 to 3:1, the cranberry extract, the D-mannose and the guar gum are in a weight ratio of 1:1:1 and the FOS and the cranberry extract are in a weight ratio of 5:1.

\* \* \* \* \*